(12) United States Patent
Bhandari

(10) Patent No.: US 11,377,657 B2
(45) Date of Patent: Jul. 5, 2022

(54) COMPOSITIONS AND METHODS OF INHIBITING GENE EXPRESSION IN A LUNG

(71) Applicant: Vineet Bhandari, Lansdale, PA (US)

(72) Inventor: Vineet Bhandari, Lansdale, PA (US)

( * ) Notice: Subject to any disclaimer, the term of this patent is extended or adjusted under 35 U.S.C. 154(b) by 0 days.

(21) Appl. No.: 16/883,667

(22) Filed: May 26, 2020

(65) Prior Publication Data
US 2021/0261967 A1 Aug. 26, 2021

Related U.S. Application Data

(60) Division of application No. 16/233,346, filed on Dec. 27, 2018, now abandoned, which is a continuation of application No. 14/743,519, filed on Jun. 18, 2015, now abandoned.

(60) Provisional application No. 62/015,032, filed on Jun. 20, 2014.

(51) Int. Cl.
| | |
|---|---|
| *C07H 21/04* | (2006.01) |
| *C12N 15/113* | (2010.01) |
| *A61K 9/00* | (2006.01) |
| *A61K 31/713* | (2006.01) |
| *A61K 45/06* | (2006.01) |
| *C12N 15/11* | (2006.01) |
| *A61K 47/24* | (2006.01) |

(52) U.S. Cl.
CPC ........ *C12N 15/1136* (2013.01); *A61K 9/0043* (2013.01); *A61K 9/0073* (2013.01); *A61K 31/713* (2013.01); *A61K 45/06* (2013.01); *C12N 15/111* (2013.01); *C12N 15/113* (2013.01); *A61K 47/24* (2013.01); *C12N 2310/113* (2013.01); *C12N 2310/14* (2013.01); *C12N 2320/30* (2013.01); *C12N 2320/32* (2013.01)

(58) Field of Classification Search
None
See application file for complete search history.

(56) References Cited

U.S. PATENT DOCUMENTS

| 7,683,036 B2 | 3/2010 | Bennet et al. |
|---|---|---|
| 2007/0015788 A1 | 1/2007 | Cumming et al. |
| 2007/0281900 A1 | 12/2007 | Cui et al. |
| 2007/0293449 A1 | 12/2007 | Cui et al. |
| 2009/0306194 A1* | 12/2009 | Ford ............ A61K 9/0019 514/44 R |
| 2011/0014133 A1 | 1/2011 | Grunstein |
| 2011/0119781 A1 | 5/2011 | Bramlage et al. |
| 2012/0022138 A1 | 1/2012 | Santel et al. |
| 2012/0289584 A1 | 11/2012 | Cui et al. |
| 2013/0225655 A1 | 8/2013 | Lu et al. |

OTHER PUBLICATIONS

Choo-Wing, Rayman, et al. ("Hyperoxia and interferon-γ-induced injury in developing lungs occur via cyclooxygenase-2 and the endoplasmic reticulum stress-dependent pathway." American journal of respiratory cell and molecular biology 48.6 (2013): 749-757, originally published Mar. 7, 2013.*
Ramirez, John Gregory. ("Surfactant Enhanced Delivery Of C/ebp Homologous Protein And Angiopoietin 2 Silencing RNA To Prevent Bronchopulmonary Dysplasia In Mouse Lung." Jan. 2014).*
D'Alessandro-Gabazza CN, et al., "Development and preclinical efficacy of novel transforming growth factor-β1 short interfering RNAs for pulmonary fibrosis", Am J Respir Cell Mol Biol. 46(3), Mar. 2012, 397-406.
Harijith, et al. "A role for matrix metalloproteinase 9 in IFNγ-mediated injury in developing lungs: relevance to bronchopulmonary dysplasia", Am J Respir Cell Mol Biol. 44(5), May 2011, 621-630.
Li, et al. "A potential role of the JNK pathway in hyperoxia-induced cell death, myofibroblast transdifferentiation and TGF-β1-mediated injury in the developing murine lung", BMC Cell Biol. 12(54), Dec. 15, 2011.
Chowdhury, Badrul (Center for Drug Evaluation and Research 021746Orig1s000 Mar. 6, 2012).
Syed, Mansoor, et al. "Hyperoxia causes miR-34a-mediated injury via angiopoietin-1 in neonatal lungs." Nature Communications 8.1 (2017): 1117-1189.
Bhandari, Vineet, et al. "Hyperoxia causes angiopoietin 2-mediated acute lung injury and necrotic cell death." Nature Medicine 12.11 (2006): 1286-1293.
Choo-Wing, Rayman, et al. "Hyperoxia and interferon-γ-induced injury in developing lungs occur via cyclooxygenase-2 and the endoplasmic reticulum stress-dependent pathway." American Journal of Respiratory Cell and Molecular Biology 48.6 (2013): 749-757.
Li, X. J. et al. "MicroRNA-34a: a potential therapeutic target in human cancer." Cell Death & Disease 5.7 (2014): e1327 (8 pages).
Choo-Wing, Rayman, et al. "Developmental differences in the responses of IL-6 and IL-13 transgenic mice exposed to hyperoxia." American Journal of Physiology-Lung Cellular and Molecular Physiology 293.1 (2007): L142-L150.
Parra, Elisa, et al. "A combined action of pulmonary surfactant proteins SP-B and SP-C modulates permeability and dynamics of phospholipid membranes." Biochemical Journal 438.3 (2011): 555-564.

(Continued)

*Primary Examiner* — Kimberly Chong
(74) *Attorney, Agent, or Firm* — Mendelsohn Dunleavy, P.C.

(57) ABSTRACT

The present invention provides compositions and methods for delivery to a lung tissue comprising a small interfering RNA (siRNA) capable of inhibiting expression of a gene, and a surfactant. In one aspect, a non-polymeric methods composition comprising a small interfering RNA (siRNA) capable of inhibiting expression of a gene, and a surfactant is disclosed. In other aspects, a method of inhibiting gene expression in a lung of a subject in need thereof and treating bronchopulmonary dysplasia in a lung of a subject also disclosed. The methods comprise administering a therapeutically effective amount of a non-polymeric composition to the lung of the subject, wherein the non-polymeric composition comprises a small interfering RNA (siRNA) capable of inhibiting expression of a gene, and a surfactant.

21 Claims, 21 Drawing Sheets
Specification includes a Sequence Listing.

(56) References Cited

OTHER PUBLICATIONS

Bernhard, Wolfgang, et al. "Commercial versus Native Surfactants: Surface Activity, Molecular Components, and the Effect of Calcium" American Journal of Respiratory and Critical Care Medicine 162.4 (2000): 1524-1533.
Zysman-Colman, Zofia, et al. "Bronchopulmonary dysplasia—trends over three decades." Paediatrics & Child Health 18.2 (2013): 86-90.
Stark, Margareta, et al. "Determination of Proteins, Phosphatidylethanolamine, and Phosphatidylserine in Organic Solvent Extracts of Tissue Material by Analysis of Phenylthiocarbamyl Derivatives." Analytical Biochemistry 265. AB982856 (1998): 97-102.
Sardesai, Smeeta, et al. "Evolution of surfactant therapy for respiratory distress syndrome: past, present, and future." Pediatric Research 81.1 (2017): 240-248.
Curstedt, Tore, et al. "Low-molecular-mass surfactant protein type 1: The primary structure of a hydrophobic 8-kDa polypeptide with eight half-cystine residues." European journal of biochemistry 172.3 (1988): 521-525.
Robertson, Bengt. "Lung surfactant for replacement therapy." Clinical Physiology 3.6 (1983): 97-110.
Rudiger, Mario, et al. "Naturally derived commercial surfactants differ in composition of surfactant lipids and in surface viscosity." American Journal of Physiology-Lung Cellular and Molecular Physiology 288.2 (2005): L379-L383.
Paul, Saritha, et al. "Poractant alfa versus beractantfor respiratory distress syndrome in preterm infants: a retrospective cohort study " Journal of Paediatrics and Child Health 49.10 (2013): 839-844.
Kennedy, Kathleen A., et al. "Prevention and management of bronchopulmonary dysplasia: Lessons learned from the neonatal research network." Seminars in Perinatology 40.6 (2016): 348-355.
Lopez-Rodriguez, Elena, et al. "Structure-function relationships in pulmonary surfactant membranes: From biophysics to therapy." Biochimica et Biophysica Acta (BBA)—Biomembranes 1838.6 (2014): 1568-1585.
Johansson, Jan, et al. "Surfactant protein B: disulfide bridges, structural properties and kringle similarities." Biochemistry 30.28 (1991): 6917-6921.
Almlén, Andreas, et al. "Surfactant proteins B and C are both necessary for alveolar stability at end expiration in premature rabbits with respiratory distress syndrome." Journal of Applied Physiology 104.4 (2008): 1101-1108.
Veldhuizen, Edwin JA, et al. "The Role of Surfactant Proteins in DPPC Enrichment of Surface Films." Biophysical Journal 79.6 (2000): 3164-3171.
Hentschel, Roland, et al. "Surfactant replacement therapy: from biological basis to current clinical practice." Pediatric Research 88.2 (2020): 176-183.
Johansson, J., et al. "Synthetic surfactants with SP-B and SP-C analogues to enable worldwide treatment of neonatal respiratory distress syndrome and other lung diseases." Journal of Internal Medicine 285.2 (2019): 165-186.
Curstedt, Tore, et al. "A Unique Story in Neonatal Research: The Development of a Porcine Surfactant." Neonatology 107.4 (2015): 321-329.
Chiesi USA Inc, CUROSURF® FDA Label, Reference ID: 3642509 (2014): 6 pages.

* cited by examiner

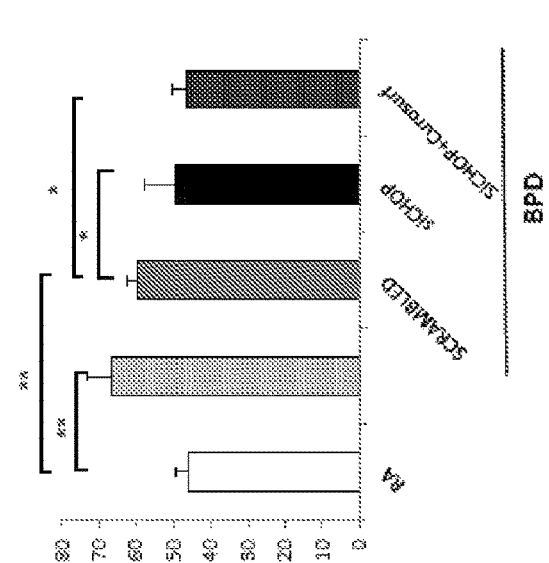
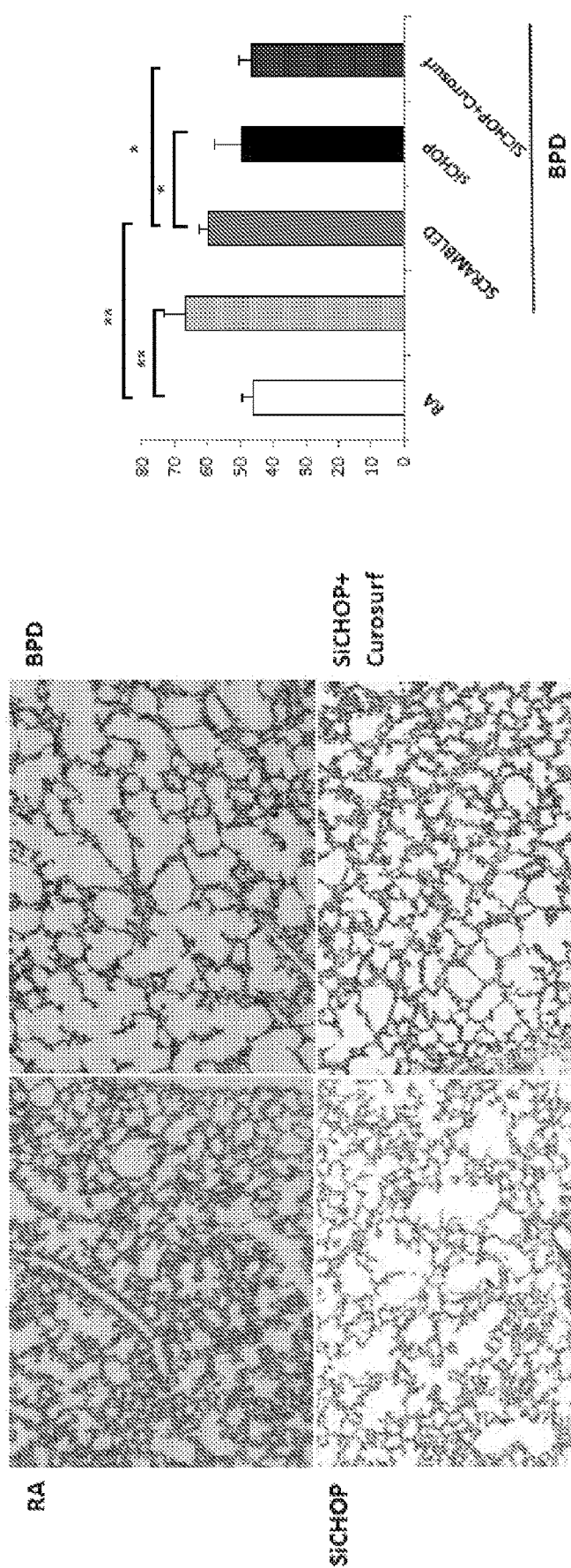
Figure 19A
Figure 19B

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1
ucaagaguag ugaaggguuut t                                            21

<210> SEQ ID NO 2
<211> LENGTH: 21
<212> TYPE: DNA
<213> ORGANISM: Artificial Sequence
<220> FEATURE:
<223> OTHER INFORMATION: Synthetic sequence

<400> SEQUENCE: 2
uugucgucug guuuaguact t                                             21
```

```
<210> SEQ ID NO 3
<211> LENGTH: 22
<212> TYPE: DNA
<213> ORGANISM: Artificial Sequence
<220> FEATURE:
<223> OTHER INFORMATION: Synthetic sequence

<400> SEQUENCE: 3
uggcaguguc uuagcugguu gu                                              22
```

COMPOSITIONS AND METHODS OF INHIBITING GENE EXPRESSION IN A LUNG

CROSS-REFERENCE TO RELATED APPLICATIONS

This application is a divisional of, and claims priority to, U.S. patent application Ser. No. 16/233,346, filed Dec. 27, 2018, which, in turn, is a continuation of, and claims priority to, U.S. patent application Ser. No. 14/743,519, filed Jun. 18, 2015, which, in turn, claims priority to U.S. Provisional Application No. 62/015,032, filed on Jun. 20, 2014, the disclosures of which are hereby incorporated by reference in their entirety herein.

STATEMENT OF RIGHTS TO INVENTIONS MADE UNDER FEDERALLY SPONSORED RESEARCH

This invention was made with government support under HL085 1 03 and HL074195, awarded by the National Institutes of Health. The government has certain rights in the invention.

BACKGROUND OF THE INVENTION

Bronchopulmonary dysplasia (BPD) is the most common chronic respiratory disease in infants and is a devastating condition that disrupts the developmental program of the lung secondary to preterm birth and an interaction between genetic-environmental factors (hyperoxia, invasive mechanical ventilation and sepsis). Although the definition of BPD has evolved over the past decade, it is currently defined as the need for oxygen supplementation for 28 days of life and a "physiologic" assessment of the oxygen (O2) requirement at 36 weeks postmenstrual age. It is estimated that 10,000-15,000 new cases of BPD occur each year in the United States, and significantly, 97% of all BPD cases occur in infants with a birth weight less than 1250 grams. Despite many advances in neonatal ventilation techniques, widespread use of surfactant and antenatal corticosteroids, as well as aggressive fluid management, the incidence of BPD has remained the same or has increased slightly.

Management of BPD takes a considerable toll on health services. Among preterm infants, the single costliest complication of hospitalization during infancy is BPD, with an average cost per discharge of $116,000. Additionally, BPD is associated with significant pulmonary and neurodevelopmental sequelae that continue to have health ramifications for the patient into adulthood. It is thus important to understand the long-term consequences of BPD, as they are likely to have a significant impact on treatment and cost and application of health care during the lifetime of those born prematurely.

To date, there is no specific and effective prevention or treatment for BPD. Therefore, a need exists in the art for compositions and methods to prevent and treat BPD in premature babies, infants and children, which prevent or treat acute lung injury in older children and adults.

SUMMARY OF THE INVENTION

As described herein, the present invention includes compositions and methods for inhibiting expression of a gene in a lung tissue. In one aspect, the invention includes a non-polymeric composition comprising a small interfering RNA (siRNA) capable of inhibiting expression of a gene, and a surfactant, wherein the composition is formulated for delivery to a lung tissue.

In another aspect, the invention includes a method of inhibiting gene expression in a lung of a subject in need thereof comprising administering a therapeutically effective amount of a non-polymeric composition to the lung of the subject, wherein the non-polymeric composition comprises a small interfering RNA (siRNA) capable of inhibiting expression of a gene, and a surfactant.

In yet another aspect, the invention includes a method of treating bronchopulmonary dysplasia in a lung of a subject comprising administering a therapeutically effective amount of a non-polymeric composition to the lung of the subject, wherein the non-polymeric composition comprises a small interfering RNA (siRNA) capable of inhibiting expression of a hyperoxia-induced gene, and a surfactant.

In various embodiments of the above aspects or any other aspect of the invention delineated herein, the siRNA comprises an RNA that inhibits expression of at least one gene encoding a protein selected from the group consisting of C/EBP homologous protein (CHOP), interferon-gamma (IFN-y), transforming growth factor-beta I (TGF-1), and angiopoietin 2 (Ang2). In another embodiment, the siRNA is selected from the group consisting of CHOP siRNA, Ang2 siRNA, and anti-sense made against the mature miRNA34a sequence. In still another embodiment, the siRNA is selected from the group consisting of SEQ ID NO:1, SEQ ID NO:2, and SEQ ID NO:3. In yet another embodiment, the siRNA is an antagomir, such as a miR34a antagomir. In still another embodiment, the siRNA comprises an RNA that inhibits expression of at least one gene encoding an anti-inflammatory protein selected from the group consisting of Sirt1, Bcl2, Ang1, Tie2, Akt, DLLI, Notch 1, Notch 2, CDK4, Cyclin DI, caspase 3, caspase 8, caspase 9, Fas, and Fas-L.

In some embodiments of the above aspects or any other aspect of the invention delineated herein, the surfactant comprises a phospholipid. In one embodiment, the phospholipid comprises phosphotidylcholine or derivatives thereof.

In another embodiment, the composition is formulated for intranasal or inhalation administration. In one embodiment, the composition is delivered to alveoli in the lung.

In some embodiments of the above aspects or any other aspect of the invention delineated herein, the composition further comprises an inhibitor of cox-2.

In one embodiment, the invention includes assessing dysregulated vascularization in the lung.

In another embodiment, the lung is hyperoxic.

In yet another embodiment, the subject has at least one of bronchopulmonary dysplasia and hyperoxia-induced cell death in the lung.

BRIEF DESCRIPTION OF THE DRAWINGS

FIG. 19A is a panel of images showing lung histology in newborn WT mice administered CHOP siRNA alone or with surfactant (Curosurf®) as the delivery vehicle in the BPD mouse model at PN14. CHOP siRNA with or without surfactant was delivered intranasally on PN1, with repeat doses on PN3 and PN4. Control mice were kept in RA from birth until PN14. Representative photomicrographs of mouse lungs (H&E stain) at PN14 are shown at low-magnification (10×).

FIG. 19B is a graph showing lung morphometry (chord length) in newborn WT mice administered CHOP or scrambled siRNA alone or with surfactant (Curosurf®) as the delivery vehicle in the BPD mouse model at PN14. Scrambled or CHOP siRNA was delivered intranasally on PN1, with repeat doses on PN3 and PN4. Control mice were kept in RA from birth until PN14. *P:S 0.05, **P:S 0.01. RA: room air; siCHOP: CHOP siRNA.

DETAILED DESCRIPTION OF THE INVENTION

Definitions

Figure 1:
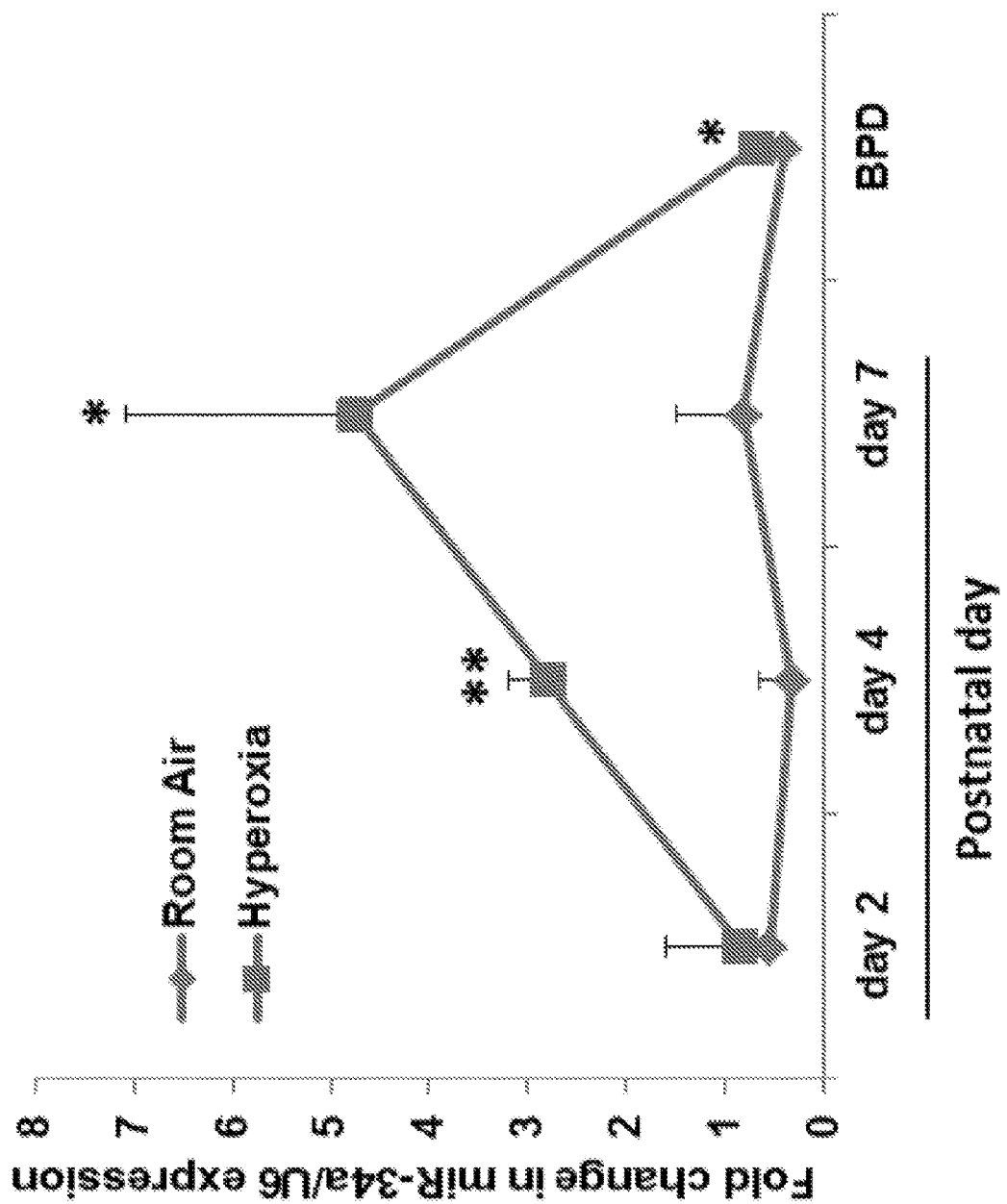
FIG. 1 is a diagram showing time-course expression of the mature form of micro RNA (miR) 34a in lungs of newborn mice exposed to hyperoxia and the BPD model. C57B16/J newborn mice were exposed to hyperoxia (100% $O_2$) or room air from post natal day (PN)1-7, and sacrificed at specified time points. The hyperoxia-induced BPD mouse model was generated-by exposing newborn mice to hyperoxia from PNI-4, followed by recovery in room air from PN5 to PN14. Mice were sacrificed and lungs removed for RNA extraction. Estimation of miR34a was done by real-time PCR. BPD corresponds to PN14.*p<0.05; **p:S0.001.

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or within 10%, 9%, 8%, 7%, 6%, 5%, 4%, 3%, 2%, 1%, 0.5%, 0.1%, 0.05%, or 0.01% of the specified value, as such variations are appropriate to perform the disclosed methods. Unless otherwise clear from context, all numerical values provided herein may be modified by the term about.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "alveoli" is meant a cellular air sac at the terminal end of the respiratory tract. Epithelial cells, such as type I and type II alveolar cells, form the structure of the alveoli and are interspersed with capillaries for gas exchange.

By "antagomir" is meant anti-miRs or blocking oligo-nucleotides that prevent other molecules from binding a mRNA molecule. Antagomirs are small synthetic RNAs that are complementary to a miRNA target to silence endogenous miRNA. The antagomir may include modifications to prevent degradation and/or mispairings to prevent enzymatic cleavage. In one embodiment, the antagomir is a miR34a antagomir.

By "biomarker" or "marker" is meant any protein or polynucleotide having an alteration in expression level or activity that is associated with a disease or disorder.

By "bronchopulmonary dysplasia" or "BPD" is meant a chronic lung condition, disorder or disease that most commonly affects infants and children, characterized by abnormal alveolarization or injury to microvasculature that results in reduction of overall surface area for sufficient gas exchange.

By "complementary sequence" or "complement" is meant a nucleic acid base sequence that can form a double-stranded structure by matching base pairs to another polynucleotide sequence. Base pairing occurs through the formation of hydrogen bonds, which may be Watson-Crick, Hoogsteen or reversed Hoogsteen hydrogen bonding, between complementary nucleobases. For example, adenine and thymine are complementary nucleobases that pair through the formation of hydrogen bonds.

By "disorder" is meant any condition or disease that damages or interferes with the normal function of a cell in a lung, a lung tissue, or an organ of the respiratory system. Examples of disorders include respiratory distress syndrome (RDS), tachypnea, tachycardia, frequent desaturations, pulmonary hypoplasia, dysregulated vascularization, or the like.

By "dysregulated vascularization" is meant dysfunctional, abnormal or inhibition of blood vessels or capillaries formation in the lung, such as the alveoli.

By "effective amount" is meant the amount required to reduce or improve at least one symptom of a disease relative to an untreated patient. The effective amount of active compound(s) used to practice the present invention for therapeutic treatment of a disease varies depending upon the manner of administration, the age, body weight, and general health of the subject.

The term "expression" as used herein is defined as the transcription and/or translation of a particular nucleotide sequence driven by its promoter.

By "fragment" is meant a portion of a polynucleotide or nucleic acid molecule. This portion contains, preferably, at least 10%, 20%, 30%, 40%, 50%, 60%, 70%, 80%, or 90% of the entire length of the reference nucleic acids. A fragment may contain 10, 20, 30, 40, 50, 60, 70, 80, 90, or 100, 200, 300, 400, 500, 600, 700, 800, 900, 1000, 1500, 2000 or 2500 (and any integer value in between) nucleotides. The fragment, as applied to a nucleic acid molecule, refers to a subsequence of a larger nucleic acid. A "fragment" of a nucleic acid molecule may be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

By "hyperoxic" or "hyperoxia" is meant an excess of oxygen or higher than normal partial pressure (atmospheric) of oxygen. Hyperoxia in the lung can lead to oxygen toxicity, cellular damage, and lung injury.

By "hyperoxia-induced gene" is meant a gene whose expression is induced, either directly or indirectly, under hyperoxic conditions. Examples of such hyperoxia-induced genes include, but are not limited to C/EBP homologous protein (CHOP), interferon-gamma (IFN-y), transforming growth factor-beta I (TGF-1), and angiopoietin 2 (Ang2), and anti-inflammatory proteins such as Sirt1, Bcl2, Tie2, Akt, DLLI, Notch 1, Notch 2, CDK4, Cyclin DI, caspase 3, caspase 8, caspase 9, Fas, and Fas-L, or any combination thereof.

As used herein, the term "inhibit" is meant to refer to a decrease in biological state. For example, the term "inhibit" may be construed to refer to the ability to negatively regulate the expression, stability or activity of a protein, including but not limited to transcription of a protein mRNA, stability of a protein mRNA, translation of a protein mRNA, stability of a protein polypeptide, a protein post-translational modifications, a protein activity, a protein signaling pathway or any combination thereof.

Further, the term "inhibit" may be construed to refer to the ability to negatively regulate the expression, stability or activity of a miRNA, wherein such inhibition of the miRNA may affect modulation of a gene, protein mRNA, stability of a protein mRNA, translation of a protein mRNA, stability of a protein, a protein post-translational modifications, and/or a protein activity.

"Instructional material," as that term is used herein, includes a publication, a recording, a diagram, or any other medium of expression that may be used to communicate the usefulness of the compounds of the invention. In some instances, the instructional material may be part of a kit useful for effecting alleviating or treating the various diseases or disorders recited herein. Optionally, or alternately, the instructional material may describe one or more methods of alleviating the diseases or disorders in a cell or a tissue of a mammal. The instructional material of the kit may, for example, be affixed to a container that contains the compounds of the invention or be shipped together with a container that contains the compounds. Alternatively, the instructional material may be shipped separately from the container with the intention that the recipient uses the instructional material and the compound cooperatively. For example, the instructional material is for use of a kit; instructions for use of the compound; or instructions for use of a formulation of the compound.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "microRNA" or "miRNA" or "miR" is meant a small non-coding RNA, which functions in transcriptional and/or post-transcriptional regulation of gene expression.

By "non-polymeric" is meant to lack a fixed or cross-linked polymer network made up of synthetic or biomolecular repeating units. In one embodiment, a composition is non-polymeric when it lacks a fixed or crosslinked polymer network, such as lacking a hydrogel, nano- or micro-particle or gel, nano- or micro-molecule, or similar component.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutical composition" or "pharmaceutically acceptable composition" refers to a mixture of at least one compound or molecule useful within the invention with a pharmaceutically acceptable carrier. The pharmaceutical composition facilitates administration of the compound or molecule to a patient. Multiple techniques of administering a compound or molecule exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or molecule useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

By "phospholipid" is meant a molecule with a hydrophilic phosphate group connected to a hydrophobic lipid. Examples of a phospholipid include, but are not limited to, phosphotidylcholine, phosphatidic acid, phosphatidylethanolamine, phosphatidylserine, a phosphoinositide such as phosphatidylinositol, phosphatidylinositol phosphate, a phosphosphingolipid such as ceramide phosphorylcholine, ceramide phosphorylethanolamine, and ceramide phosphoryllipid, or any derivative thereof.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which may be hydrolyzed into the monomeric "nucleotides." The monomeric nucleotides may be hydrolyzed into nucleosides. As used herein polynucleotides include, but are not limited to, all nucleic acid sequences that are obtained by any means available in the art, including, without limitation, recombinant means, i.e., the cloning of nucleic acid sequences from a recombinant library or a cell genome, using ordinary cloning technology and PCR™, and the like, and by synthetic means. The following abbreviations for the commonly occurring nucleic acid bases are used. "A" refers to adenosine, "C" refers to cytosine, "G" refers to guanosine, "T" refers to thymidine, and "U" refers to uridine. The term "RNA" as used herein is defined as ribonucleic acid. The term "recombinant DNA" as used herein is defined as DNA produced by joining pieces of DNA from different sources.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include intrans to the extent that the nucleotide sequence encoding the protein may in some version contain an intron(s).

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

As used herein, the terms "prevent," "preventing," "prevention," and the like refer to reducing the probability of developing a disorder or condition in a subject, who does not have, but is at risk of or susceptible to developing a disorder or condition.

By "reduces" or "decreases" is meant a negative alteration of at least 10%, 25%, 50%, 75%, or 100%.

By "reference" is meant a standard or control. A "reference" is also a defined standard or control used as a basis for comparison.

As used herein, "sample" or "biological sample" refers to anything, which may contain the biomarker (e.g., polypeptide, polynucleotide, or fragment thereof) for which a biomarker assay is desired. The sample may be a biological sample, such as a biological fluid or a biological tissue. In one embodiment, a biological sample is a tissue sample including pulmonary vascular cells. Such a sample may include diverse cells, proteins, and genetic material. Examples of biological tissues also include organs, tumors, lymph nodes, arteries and individual cell(s). Examples of biological fluids include urine, blood, plasma, serum, saliva, semen, stool, sputum, cerebral spinal fluid, tears, mucus, amniotic fluid or the like.

By "small interfering RNA" or "siRNA" is meant a short RNA molecule that may be double stranded, which interferes with the expression of a specific gene that includes a nucleotide sequence complementary to the RNA molecule.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

A "subject" or "patient," as used therein, may be a human or non-human mammal. Non-human mammals include, for example, livestock and pets, such as ovine, bovine, porcine, canine, feline and murine mammals. Preferably, the subject is human.

By "surfactant" is meant a compound that lowers the surface tension between two liquids or a liquid and a solid. The surfactant is a compound that is amphiphilic with a water soluble component and a water insoluble component.

As used herein, the terms "treat," treating," "treatment," and the like refer to reducing or improving a disorder and/or symptom associated therewith. It will be appreciated that, although not precluded, treating a disorder or condition does not require that the disorder, condition or symptoms associated therewith be completely ameliorated or eliminated.

A "vector" is a composition of matter that comprises an isolated nucleic acid and that may be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression may be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Ranges provided herein are understood to be shorthand for all of the values within the range. For example, a range of 1 to 50 is understood to include any number, combination of numbers, partial integers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of an embodiment for a variable or aspect herein includes that embodiment as any single embodiment or in combination with any other embodiments or portions thereof. Any compositions or methods provided herein can be combined with one or more of any of the other compositions and methods provided herein.

Compositions

Bronchopulmonary dysplasia and related conditions and disease, such as hyperoxia, result in inflammation, dysregulated vascularization, impaired alveolarization, and injurious cell death. Blocking the deleterious effects of genes involved in inflammation, cell death and dysregulated cell proliferation is one mechanism to treat or prevent one or more symptoms of bronchopulmonary dysplasia. Compositions and methods are included herein for effective and efficient gene inhibition in a lung.

The invention includes, in one aspect, a non-polymeric composition comprising a small interfering RNA (siRNA) capable of inhibiting expression of a gene, and a surfactant, wherein the composition is formulated for delivery to a lung tissue. A non-polymeric composition lacks a fixed or cross-linked polymeric component. For example, the non-polymeric composition lacks a hydrogel, nano- or micro-particle or gel, nano- or micro-molecule, or similar component.

In one embodiment, the siRNA comprises an RNA that inhibits expression of at least one gene encoding a protein selected from the group consisting of C/EBP homologous protein (CHOP), interferon-gamma (IFN-y), transforming growth factor-beta I (TGF-1), and angiopoietin 2 (Ang2). For example, CHOP siRNA: UCAAGAGUAGUGAAG-GUUUTT; Ang2 siRNA: UUGUCGUCUGGUUU-AGUACTT; Anti-sense made against the mature miRNA34a sequence 5'-UGGCAGUGUCUUAGCUG-GUUGU-3'. In yet another embodiment, JO the siRNA is an antagomir, such as a miR34a antagomir. In still yet another embodiment, siRNA comprises an RNA that inhibits expression of at least one gene encoding an anti-inflammatory protein selected from the group consisting of Sirt1, Bcl2, Ang1, Tie2, Akt, DLLI, Notch 1, Notch 2, CDK4, Cyclin DI, caspase 3, caspase 8, caspase 9, Fas, and Fas-L.

To enhance delivery of the siRNA or increase transfection/uptake efficiency of the siRNA into lung tissue to inhibit gene expression, the composition also includes a surfactant. The surfactant can serve as a vehicle to deliver or administer the siRNA to the lung. The surfactant can include a phospholipid, such as phosphotidylcholine and derivatives thereof.

CUROSURF™ (poractant alfa) is a sterile, non-pyrogenic pulmonary surfactant intended for intratracheal use only. CUROSURF™ is an extract of natural porcine lung surfactant consisting of 99% polar lipids (mainly phospholipids) and 1% hydrophobic low molecular weight proteins (surfactant associated proteins SP-B and SP-C).

CUROSURF™ is a white to creamy white suspension of poractant alfa. Each milliliter of suspension contains 80 mg of poractant alfa (surfactant extract) that includes 76 mg of phospholipids and 1 mg of protein of which 0.45 mg is SP-B. The amount of phospholipids is calculated from the content of phosphorus and contains 55 mg of phosphatidylcholine of which 30 mg is dipalmitoylphosphatidylcholine. It is suspended in 0.9% sodium chloride solution. The pH is adjusted with sodium bicarbonate to a pH of 6.2 (5.5 to 6.5).

As it is desirable to deliver the composition to the lung, in one embodiment, the composition is formulated for intranasal delivery. In another embodiment, the composition is formulated for inhalation delivery. The composition may be aerosolized for enhanced delivery and administration.

The composition may further include additional agents and inhibitors of gene expression. In one embodiment, the composition further comprises an inhibitor of cox-2.

Pharmaceutical Compositions

The invention also encompasses the use of a pharmaceutical composition of the invention to practice the methods of the invention. Such a pharmaceutical composition may be provided in a form suitable for administration to a subject, and may be comprise one or more pharmaceutically acceptable carriers, one or more additional ingredients, or some combination of these. The at least one composition of the invention may comprise a physiologically acceptable salt, such as a compound contemplated within the invention in combination with a physiologically acceptable cation or anion, as is well known in the art.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In one embodiment, the compositions of the invention are formulated using one or more pharmaceutically acceptable excipients or carriers. In one embodiment, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002);" Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

Method of Treatment

The present invention also includes methods of treating a lung in a subject in need thereof, such as a subject with bronchopulmonary dysplasia. In one aspect, a method includes JO inhibiting gene expression in a lung of a subject in need thereof comprising administering a therapeutically effective amount of a non-polymeric composition to the lung of the subject, wherein the non-polymeric composition comprises a small interfering RNA (siRNA) capable of inhibiting expression of a gene, and a surfactant.

In another aspect, a method includes treating bronchopulmonary dysplasia in a lung of a subject comprising administering a therapeutically effective amount of a non-polymeric composition to the lung of the subject, wherein the non-polymeric composition comprises a small interfering RNA (siRNA) capable of inhibiting expression of a hyperoxia-induced gene, and a surfactant.

In one embodiment, the siRNA inhibits gene expression of at least one anti-inflammatory molecule. The anti-inflammatory molecule can be selected from the group consisting of Sirt1, Bcl2, Ang1, Tie2, Akt, DLLI, Notch 1, Notch 2, CDK4, Cyclin DI, caspase 3, caspase 8, caspase 9, Fas, and Fas-L. In another embodiment, the siRNA inhibits gene expression of hyperoxia-induced gene, an anti-inflammatory molecule, or other molecule such as C/EBP homologous protein (CHOP), interferon-gamma (IFN-y), transforming growth factor-beta I (TGF-I), angiopoietin 2 (Ang2), or any combination thereof. In another embodiment, the siRNA inhibits gene expression of at least one molecule selected from the group consisting of C/EBP homologous protein (CHOP), interferon-gamma (IFN-y), transforming growth factor-beta I (TGF-I), and angiopoietin 2 (Ang2).

When the composition is administered to the lung, the composition is formulated for such administration. In one embodiment, the administration delivers the composition to alveoli in the lung. In another embodiment, the composition is formulated for inhalation administration or intranasal administration. In some embodiment, the lung is hyperoxic, such as in a subject with bronchopulmonary dysplasia or hyperoxia-induced cell death in the lung.

In another embodiment, the method further comprises administering an inhibitor of cox-2. In yet another embodiment, the method further comprises assessing dysregulated vascularization in the lung.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out embodiments of the present invention, and are not to be construed as limiting in anyway.

The Materials and Methods used in the performance of the experiments disclosed herein are now described.

Transgenic Mice

C57BL6/J mice were uses in the experimental studies. IFNy overexpressing triple transgenic (TTG) CC10-rtTA/ tTs-IFNy mice were generated in the laboratory (Am J Respir Cell Mol Biol. 2011 May; 44(5):621-30. Epub 2011 Jan. 7). TGF-1 transgenic (TG) mice had "human" TGF-1 targeted to the lung using the CC10 promoter and was "turned on" with maternal exposure to doxycycline (dox) in the drinking water, leading to transmammary activation in the TG (+) pups, as described previously (BMC Cell Biol. 2011 Dec. 15; 12:54).

Dox Water Administration

Lactating dams of newborn mice were given either regular water or dox water (0.5 g/L) from PN1 through PN7, which allowed transmammary activation of IFNy in the newborn lung, until sacrificed. Both groups i.e. WT and IFNy TTG had dox water, and regular water controls.

Western Blot Analysis

CHOP and Ang2 protein was detected with -actin as control, from lung lysates using Western analysis.

Histologic Analysis

Animals were euthanized, a median sternotomy was performed, and right heart perfusion was accomplished with calcium and magnesium-free PBS to clear the pulmonary intravascular space. The heart and lungs were then removed en bloc, then fixed to pressure (25 cm) with neutral-buffered 10% Formalin, fixed overnight in 10% Formalin, embedded in paraffin, sectioned at 5 µm, and stained. Hematoxylin and eosin stains were performed.

Morphometric Analysis

Alveolar size was estimated from the mean cord length of the airspace as described previously (Am J Respir Cell Mol Biol. 2011 May; 44(5):621-30. Epub 2011 Jan. 7). At least four animals were studied at each time point in the presence and absence of dox water. Chord length increases with alveolar enlargement.

Oxygen Exposure

For the exposure to hyperoxia (100% $O_2$), newborn mice (along with their mothers) were placed in cages in an airtight Plexiglas chamber (55×40×50 cm) as described previously (Am J Respir Cell Mol Biol. 2011 May; 44(5):621-30. Epub 2011 Jan. 7). Exposure to oxygen was initiated on PN1 of life. Two lactating dams were used. Mothers were alternated in hyperoxia and room air every 24 h. The litter size was kept limited to 12 pups to control for the effects of litter size on nutrition and growth. Throughout the experiment, they were given free access to food and water. Oxygen levels were constantly monitored by an oxygen sensor that was connected to a relay switch incorporated into the oxygen supply circuit. The inside of the chamber was kept at atmospheric pressure, and mice were exposed to a 12 h light-dark cycle.

Mouse Model of BPD

Newborn WT mice were exposed to hyperoxia, as described herein, from PN1-4 (saccular stage of murine lung development) and allowed to recover in room air for the next 10 days. Mice were sacrificed on PN14. NB WT mouse lungs at PN14 have the phenotype mimicking human BPD. For the Cox2 inhibition experiments, NB WT mice were injected daily with the celecoxib 20 mg/kid for 14 days.

Preparation and Administration of CHOP siRNA, Ang2 siRNA and miR34a Antagomir with Surfactant (Curosurf®). as the Delivery Vehicle For In Vitro Experiments:

For CHOP and Ang2 silencing in MLE12 cells, $2 \times 10^5$ cells per well were plated into six-well plates and grown overnight until they were 50-80% confluent. CHOP, Ang2 and scrambled siRNA were transfected by lipofectamine 2000 or given with or without surfactant (Curosurf®). Cells were used after 24 h for the hyperoxia experiments.

For In Vivo Experiments:

CHOP siRNA (SEQ ID NO:1, UCAAGAGUAGU-GAAGGUUUTT), Ang2 siRNA (SEQ ID NO:2, UUGUC-GUCUGGUUUAGUACTT) or miR34a-antagomir (SEQ ID NO:3, UGGCAGUGUCUUAGCUGGUUGU) was suspended in nuclease free water to make a 20 µM final concentration. Surfactant (Curosurf®) was used as the delivery vehicle in a volume of 5 µl. The newborn mouse was held by its ears and 1-2 µl per nostril of the mix was gradually released into the nostrils with the help of a long tipped micropipette. The rate of release was adjusted so as to allow the mouse to inhale the solution without trying to form bubbles. The mouse was held in the hanging position for another couple of minutes till its breathing gradually returned to normal. The control mice were administered Scrambled siRNA of the same concentration intranasally at the same volume. The doses of CHOP siRNA, Ang2siRNA or miR34a-antagomir and scrambled siRNA were administered on PN1 and PN3 in the mouse model of BPD.

Human Lung Samples of BPD

Human lung tissue samples were obtained postmortem from fetuses and premature infants having the diagnoses of respiratory distress syndrome 1-2 days (RDS 1-2), RDS 3-7 days (RDS 3-7), RDS>7 days (RDS>7), BPD and term infants as controls.

The Results of the experiments disclosed herein are now described.

The miR profile of BPD remains largely unexamined. Because miRs regulate multiple cellular functions critical for organ development and disease conditions, it is possible that miR could be a "master" regulator for a complex disorder such as BPD. Recently, miR34a expression has been noted in the hyperoxia-exposed lungs of rat and mouse and in human asthma, a condition to which BPD patients appear to be predisposed long-term. In addition, miR34a has been detected in serum and other body fluids of humans, underscoring its potential as a diagnostic and prognostic biomarker. miR34 has not been implicated in human BPD.

Figure 2A:
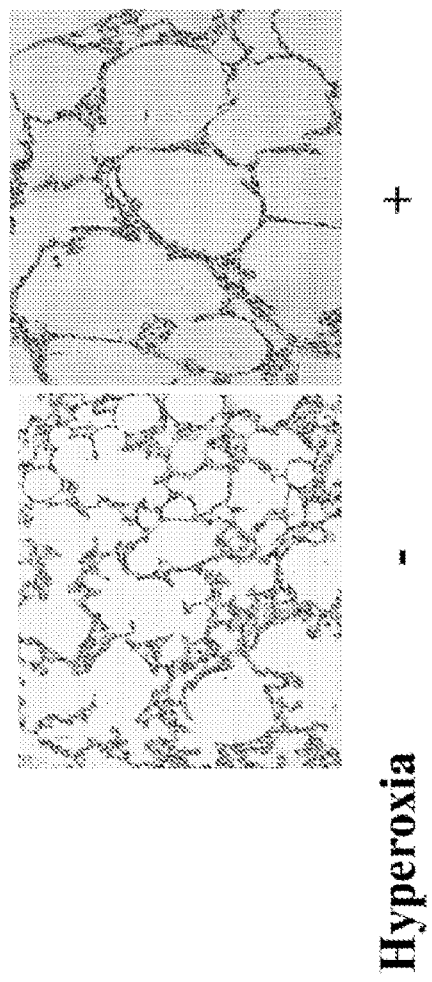
FIG. 2A is a panel of images showing the absence (left image) or presence (right image) of the effects of hyperoxia in the lungs of a hyperoxia-induced BPD mouse model.
Figure 2B:
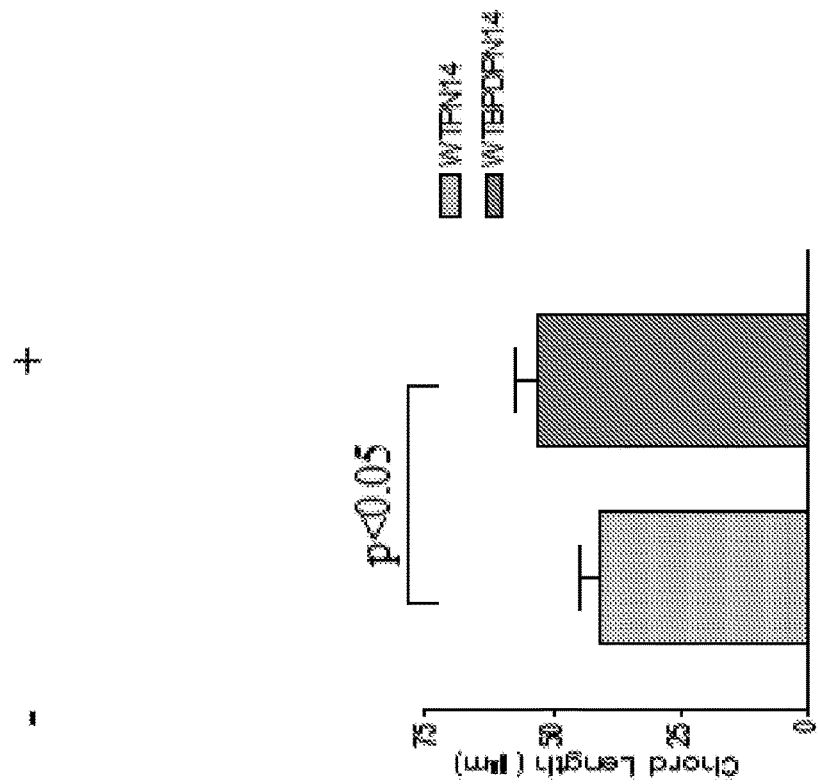
FIG. 2B is a graph showing the chord length (an indicator of mean alveolar size) in newborn wild type (WT) mice or hyperoxia-induced BPD mice at PN14.

In the experiment illustrated in FIGS. 2A and 2B, a hyperoxia-induced mouse model of BPD was used to carry out initial in vivo studies of miR34a. In this experiment, newborn mice pups were exposed to hyperoxia (100% oxygen) from postnatal stage PN1 to PN4, a timeframe that corresponds to the saccular stage of lung development and is equivalent to human premature infants at 23-28 weeks of gestation, when BNP begins to develop. The mice were then allowed to recover in room air from PN5 to PN14, which corresponds to the alveolar stage of development and is equivalent to human premature infants after 32-36 weeks of gestation, at which point the development of BPD was well underway. When mice were sacrificed at PN14, the lungs had a clearcut BPD phenotype. If the mice were allowed to live to adulthood, the pulmonary phenotype of BPD persisted, mimicking the course of the disease in humans. In these experiments, a rapid induction in expression of the mature form of miR34a at PN4 was found, which increased 5-fold by PN7 (FIG. 1). FIG. 2A is a panel of images showing the absence (left image) or presence (right image) of hyperoxia in a hyperoxia-induced BPD mouse model. FIG. 2B is a graph showing the cord length (an indicator of mean alveolar size) in newborn wild type (WT) mice or hyperoxia-induced BPD mice at post natal day 14 (PN14).

Figure 3:
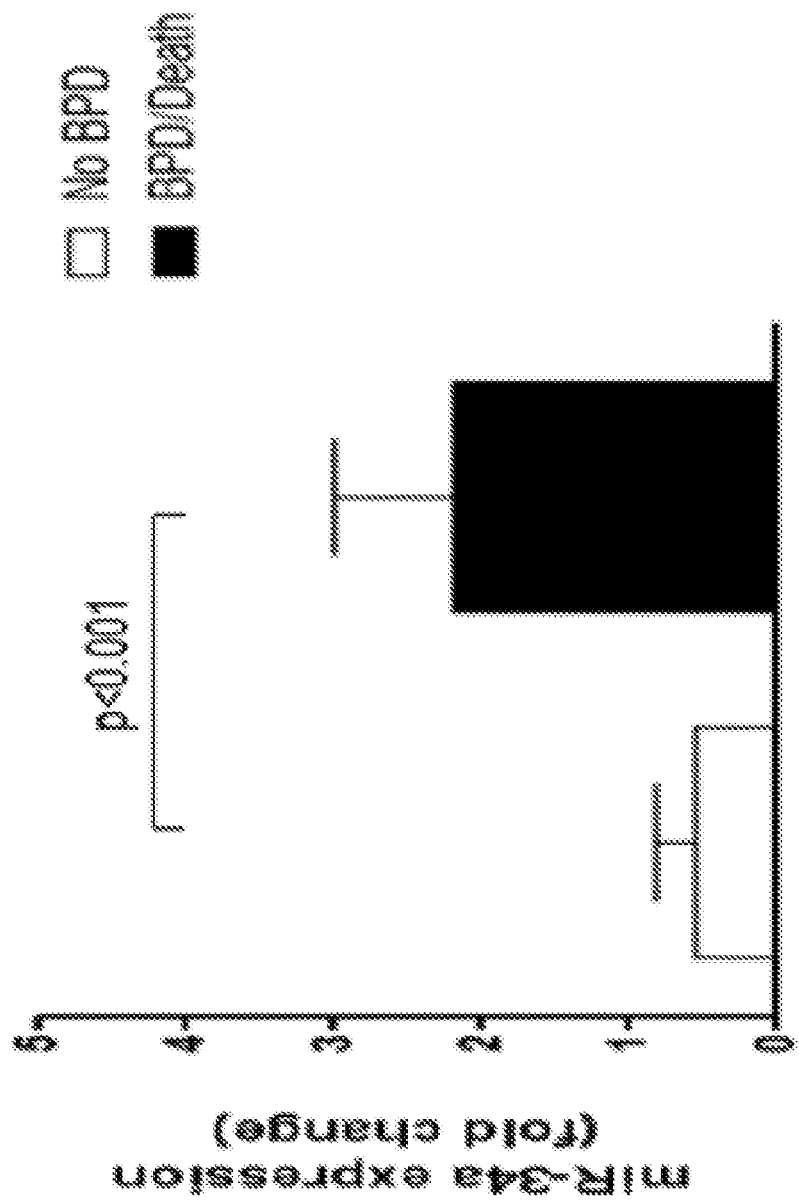
FIG. 3 is a graph showing expression of miR34a in human tracheal aspirates. Comparison of miR34a expressions in infants (n=35) with respiratory distress syndrome (RDS), who did not develop BPD (n=8; white bar) and who died/ developed BPD (n=27; black bar). Airway secretions were collected from infants who were mechanically ventilated and had endotracheal tubes in place in the first week of life. After cell separation, RNA was extracted and the expression of miR34a was measured using realtime PCR. Data expressed as mean±standard error of the mean.

Preliminary studies characterizing the expression of miR34a in human babies suffering from BPD were also analyzed. Because many infant survivors of respiratory distress syndrome (RDS) later develop BPD, neonates with RDS were analyzed for elevated levels of miR34a. To accomplish this goal, quantitative real-time PCR was used to measure miR34a expression in tracheal aspirate cell pellets from infants who had RDS severe enough to require intubation and surfactant treatment during the first week of life (n=35; 550-1250 g birth weight). The results showed a significant (p<0.001) increase in miR34a gene expression in these samples (FIG. 3).

Figure 4:
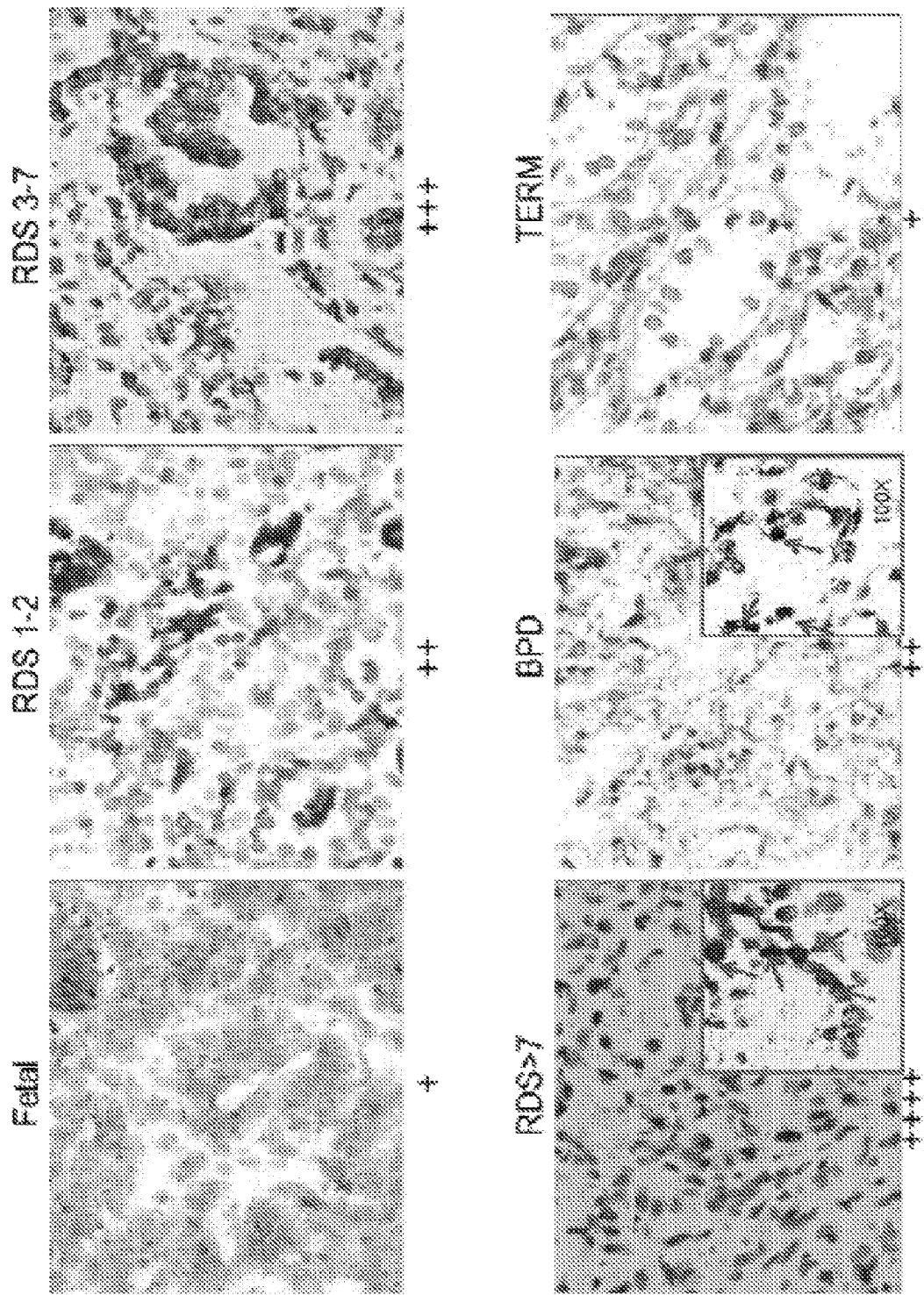
FIG. 4 is a panel of images showing in situ hybridization of miR34a (darker staining; 40×) in post-mortem lungs of premature infants at various stages of development and/or with RDS/BPD. Post-mortem samples of lungs were collected from infants with RDS, BPD, and or full-term controls of the same postnatal age. The lung samples were used to localize and quantify the degree of miR34a expression. Numbers following RDS labels on top of panels JO indicate number of days being managed for RDS prior to death. "+" to "++++" at the bottom of each panel provide a semi-quantitative assessment of miR34a expression. Arrows in the 100× insets point to Type II alveolar epithelial cells (AEC).

To determine localization of the increased miR34a expression in the lung, in situ hybridization was used to assess the expression of miR34a in lungs of human neonates at various stages of development with/without RDS and BPD. There was a substantial increase in miR34a staining in the lungs of premature infants with RDS and BPD, and it was localized to alveolar epithelial and inflammatory cells (FIG. 4). These data are consistent with mouse models and support the idea that miR34a expression in the lung during the neonatal period may have a role in BPD pathogenesis. Thus, miR34a could serve as a diagnostic/prognostic marker for BPD and could also provide a therapeutic target for this disease.

Figure 5:
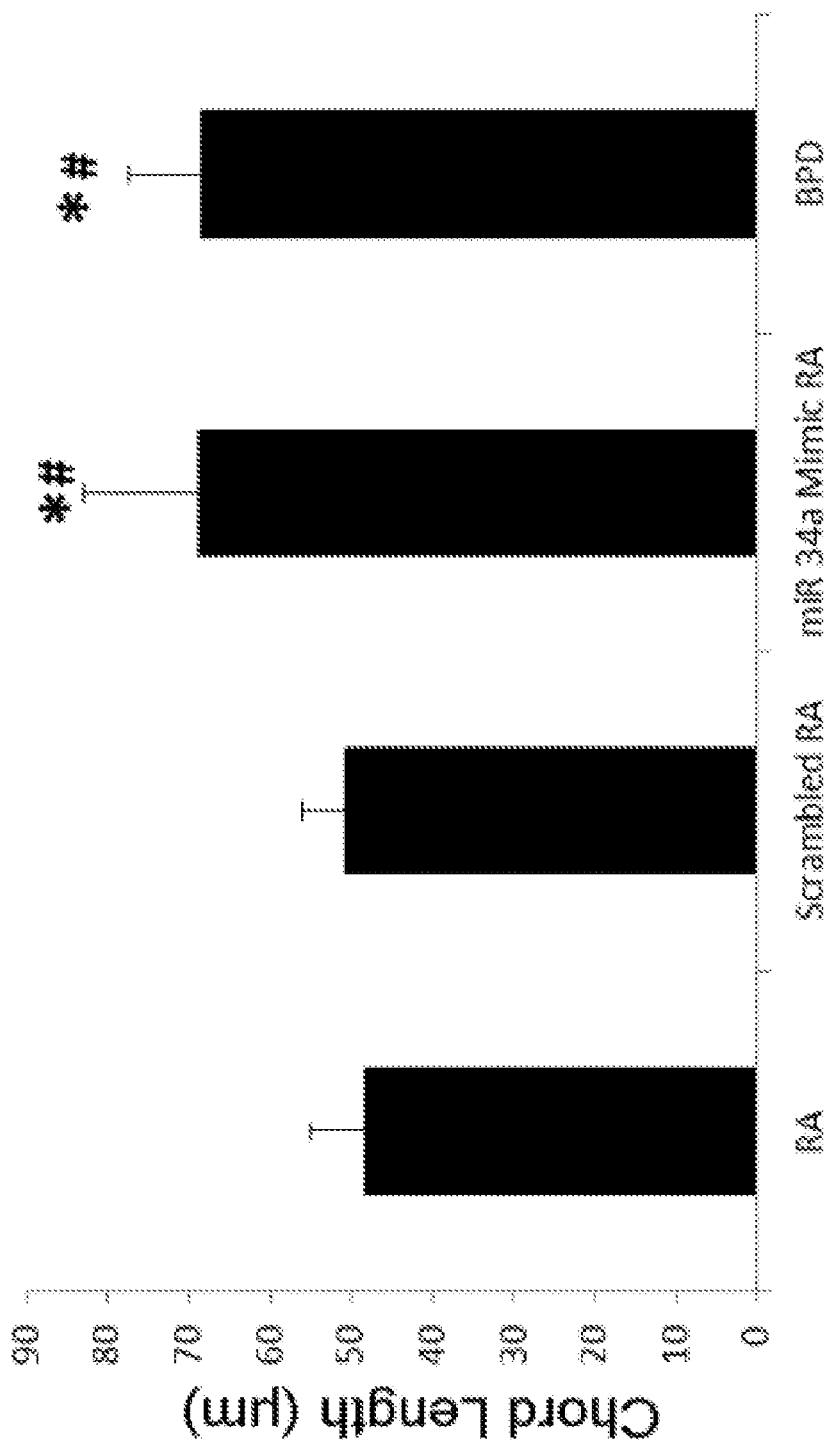
FIG. 5 is a graph showing chord length analysis in newborn WT mice administered miR34a-antagomir in room air at PN14. The miR34a-antagomir was administered on PNI and repeat doses given on PN3 and PN4. Chord length measurements (an indicator of mean alveolar size) are shown in the mice lungs administered miR34a-antagomir in RA, at PN14, along with appropriate control groups. *p<0.05 vs. RA; #p<0.05 vs. scrambled. RA: room air; Scrambled: (control) RNA with the same nucleotide composition but not the same sequence as the miR34a-antagomir; BPD: hyperoxia-exposed mouse model at PN14.
Figure 6:
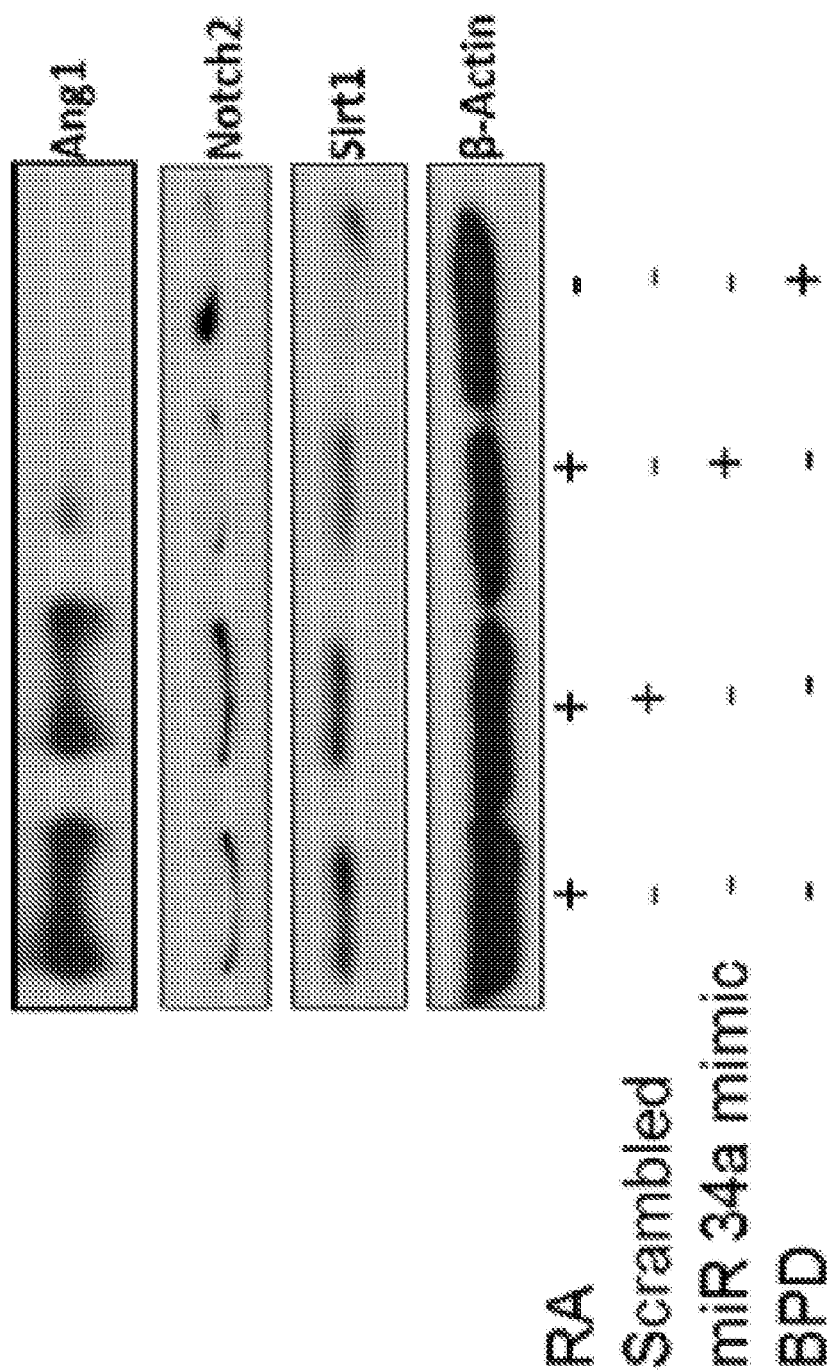
FIG. 6 is a blot showing protein expression of Ang1, Notch2, and Sirt1 in the mice lungs administered miR34a-antagomir in RA, at PN14, along with appropriate control groups. RA: room air; Scrambled: (control) RNA with the same nucleotide composition but not the same sequence as the miR34a-antagomir; BPD: hyperoxia-exposed mouse model at PN14.

To determine the role of miR34a in the development of BPD, wild-type (WT) mice were treated with miR34a-antagomir. Following treatment of normal mice in room air, chord length was measured. Longer chord length was consistent with the disrupted alveolarization that is characteristic of BPD (FIG. 5). Decreased expression levels of known down-stream targets of miR34a in the lungs of these mice were also found, including the anti-inflammatory molecule Sirtuin 1 (Sirt1), the vascular mediation Angiopoietin 1 (Ang1), and Notch2 (FIG. 6), providing further evidence of BPD pathology.

Figure 7:
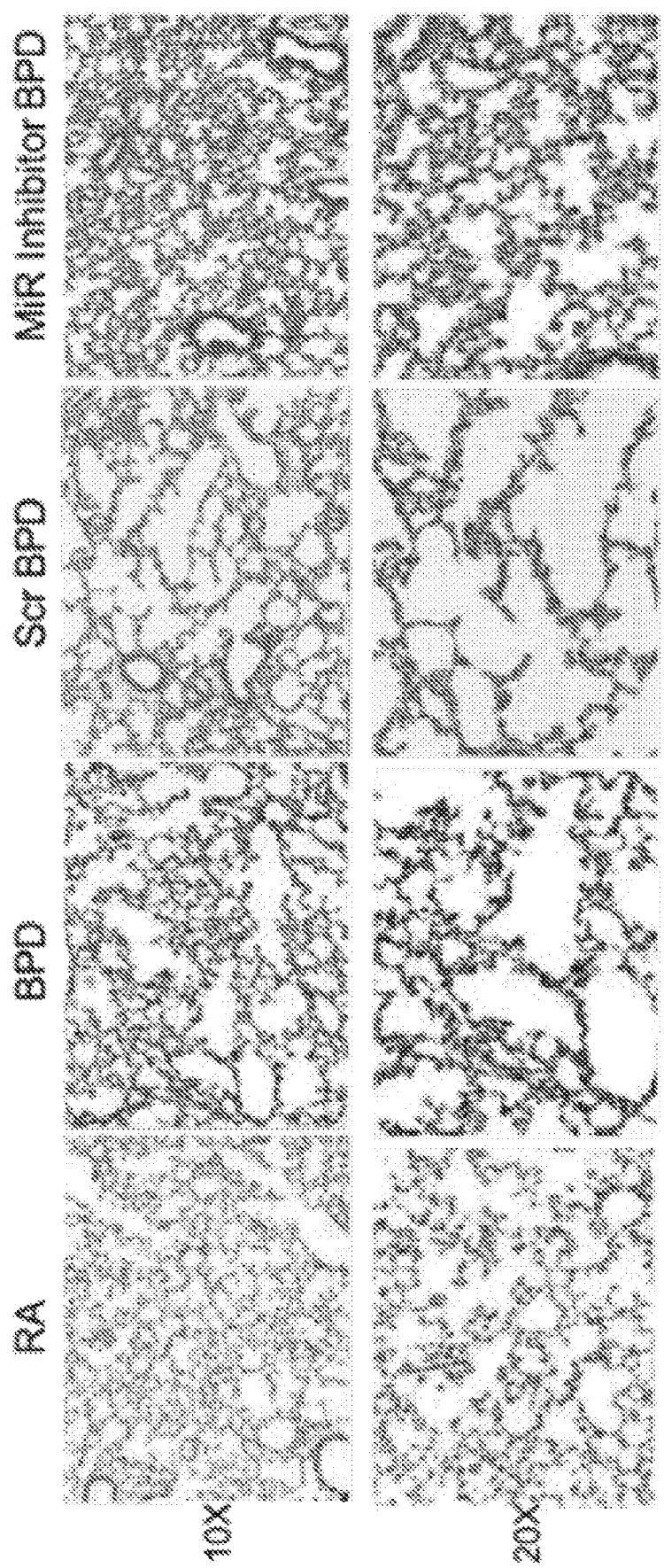
FIG. 7 is a panel of images showing lung histology and morphometry in newborn WT mice administered miR34a inhibitor in the BPD mouse model at PN14. Scrambled (Ser) or miR34a inhibitor was delivered intranasally on PNI, with repeat doses on PN3 and PN4. Control mice were kept in RA from birth until PN14. Representative photomicrographs of mouse lungs (H&E stain) at PN14 are shown at low-magnification (I Ox: top panels) and high-magnification (20×: bottom panels).
Figure 8:
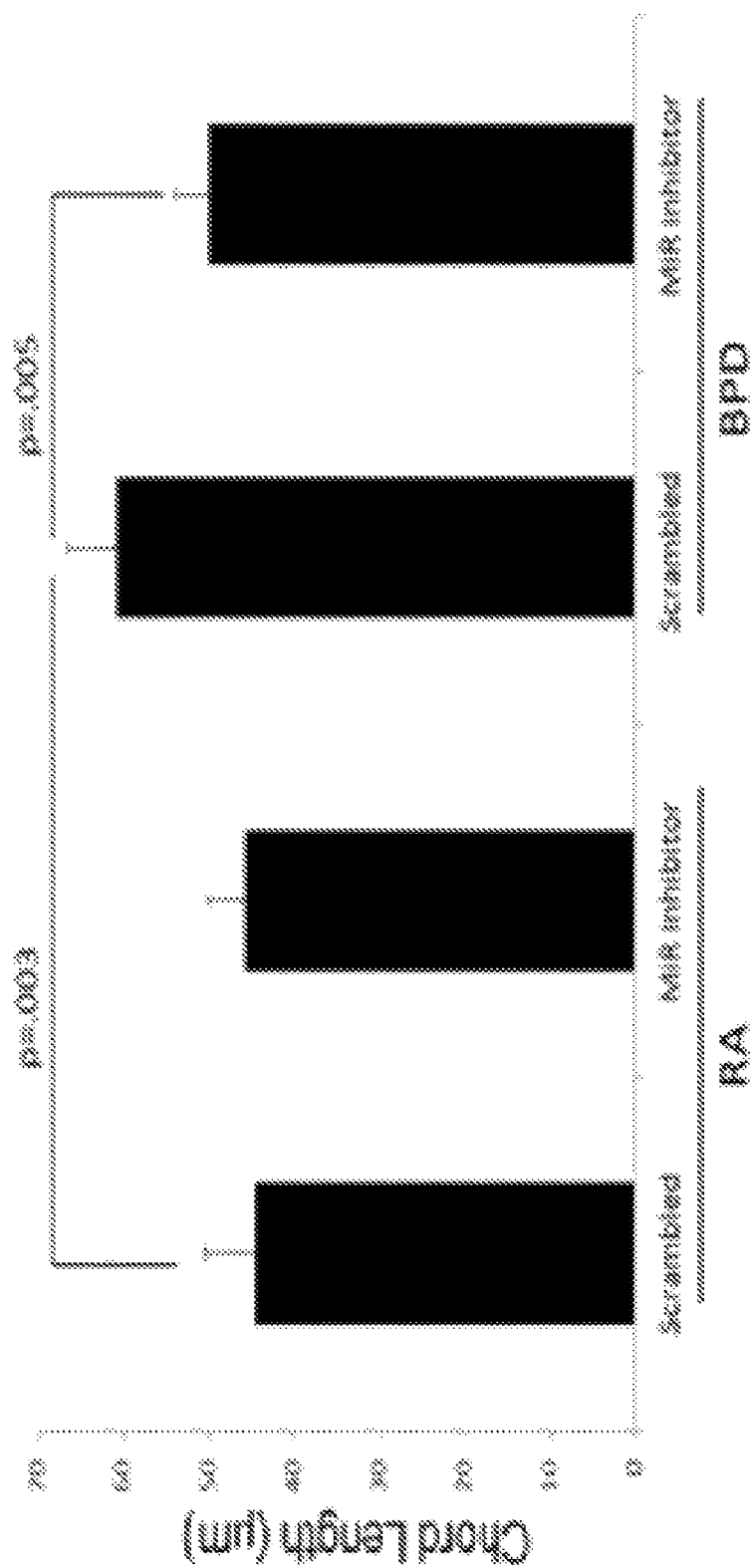
FIG. 8 is a graph showing chord length measurements in the mice lungs administered miR34a-inhibitor in the hyperoxia-induced murine BPD model, at PN14, along with appropriate control groups.

In subsequent proof-of-principle studies, the sequence of miR34a was used to generate an antisense oligonucleotide molecule, or antagomir, that inhibits miR34a. The dose was optimized to 100 nM based on in vitro testing in MLE-cells for maximal down-regulation of miR34a and used the hyperoxia-induced mouse model of BPD to test the effect of the miR34a-inhibitor in vivo. The miR34a-inhibitor was given at post-natal stage PN1 and repeated at PN3 and PN4, and histological staining (FIG. 7) and chord length measurements (FIG. 8) both showed that the miR34a-inhibitor restored the normal alveolarization in the BPD lungs.

The research has indicated that hyperoxia leads to the production and release of the mature form of miR34a. This release, in turn, increases alveolarization and leads to decreased expression of downstream miR34a targets including Ang1 (decreased expression of which is known to increase cell death in hyperoxia-induced lung injury and BPD models) and Sirt1 (which has been associated with enhanced transcription of proinflammatory mediators and BPD). The combined effect of enhanced cell death and decreased cell proliferation would be impaired alveolarization in the lung. Furthermore, it is hypothesized that miR34a enhances cell death by suppressing the Notch signaling pathway, resulting in dysregulated vascularization in the lung, one of the hallmarks of BPD.

Importantly, miRs are post-transcriptional regulators critical for organogenesis and pathogenesis, and because a single miR can target multiple functionally-related genes, miR-based therapies have the potential to be more effective than single gene approaches. For example, miR34a down-regulation (inhibition) decreases epithelial cell death (via Ang1) and inflammation (via Sirt1), while improving vascularization (via Notch2,). It seems reasonable to think that these effects, taken together, will contribute to the recovery of epithelial cells and improved alveolarization.

Figure 9:
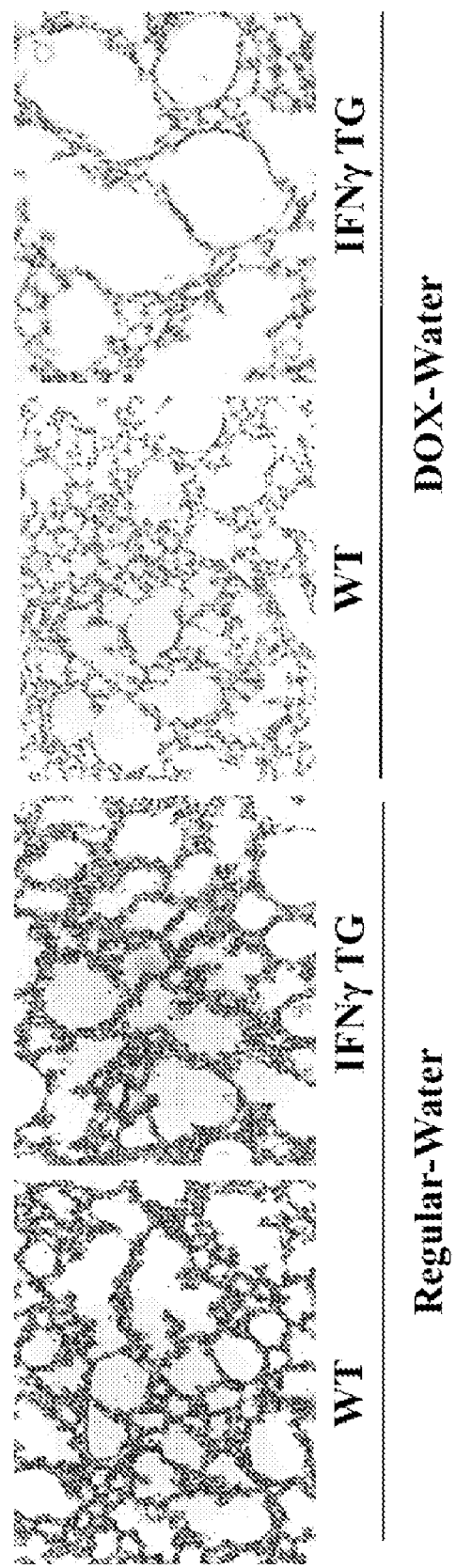
FIG. 9 is a panel of images showing lung histology and morphometry in newborn WT mice and IFN-y transgenic mice (IFN-y TG) treated with water or doxicycline (DOX) to induce expression of IFN-y which mimics the BPD mouse model at PN14 as well as humanBPD.
Figure 10B:
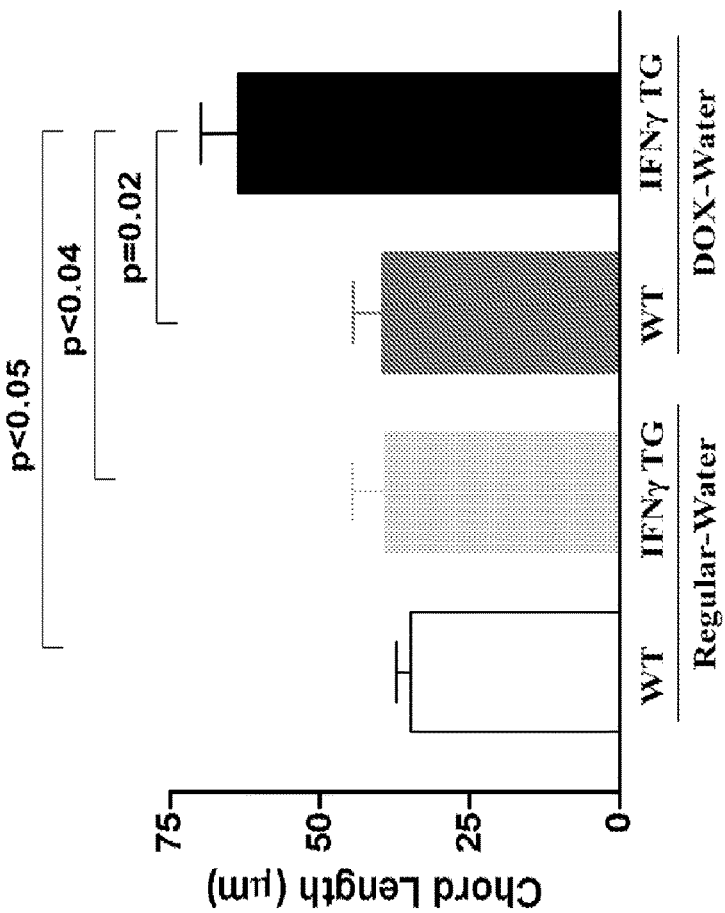
FIG. 10B is a graph showing chord length in in IFN-y TG mice treated with DOX to induce expression of IFN-y as compared to WT mice treated with water or DOX or IFN-y TG mice treated with water.
Figure 10A:
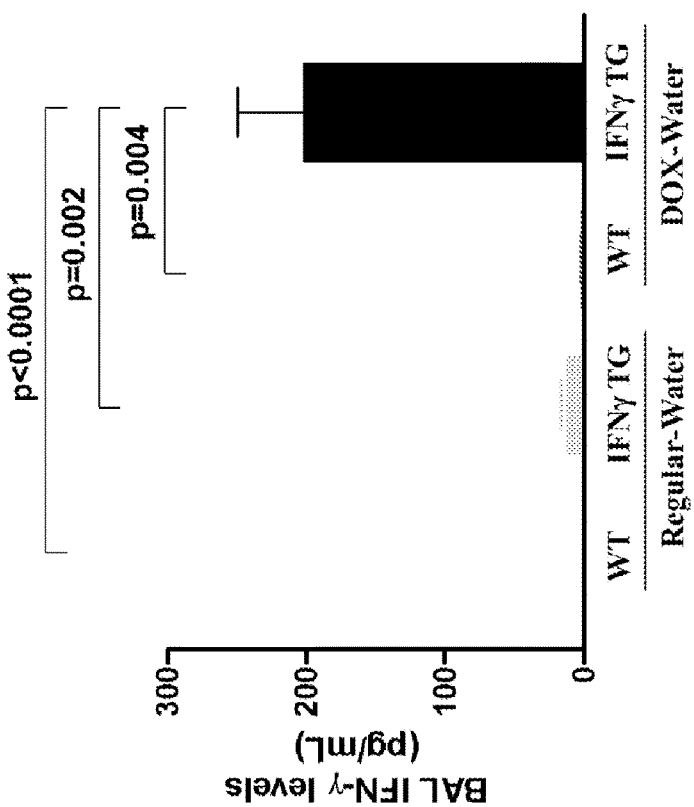
FIG. 10A is a graph showing increased levels of IFN-y in IFN-y TG mice treated with DOX to induce expression of IFN-y as compared to WT mice treated with water or DOX or IFN-y TG mice treated with water.

To determine what effects miR34a has on cell death, surfactant-enhanced delivery of siRNA directed against miR34a is being tested in 2 additional (to the hyperoxia-induced BPD model described above) models of BPD. The first is the interferon-gamma (IFN-y) inducible transgenic mice which were treated with doxycycline (DOX) to induce IFN-y. IFN-y induction in newborn mice pups was from postnatal stage PN1 to PN7, a timeframe that corresponds to the saccular/early alveolar stage of lung development and is equivalent to human premature infants at 23-30 weeks of gestation, when BPD is most likely to develop. When mice were sacrificed at PN7, the lungs had a clearcut BPD phenotype, FIG. 9. The mice had increased levels of IFN-y (FIG. 10A) and longer chord lengths (FIG. 10B), indicative of BPD.

Figure 11:
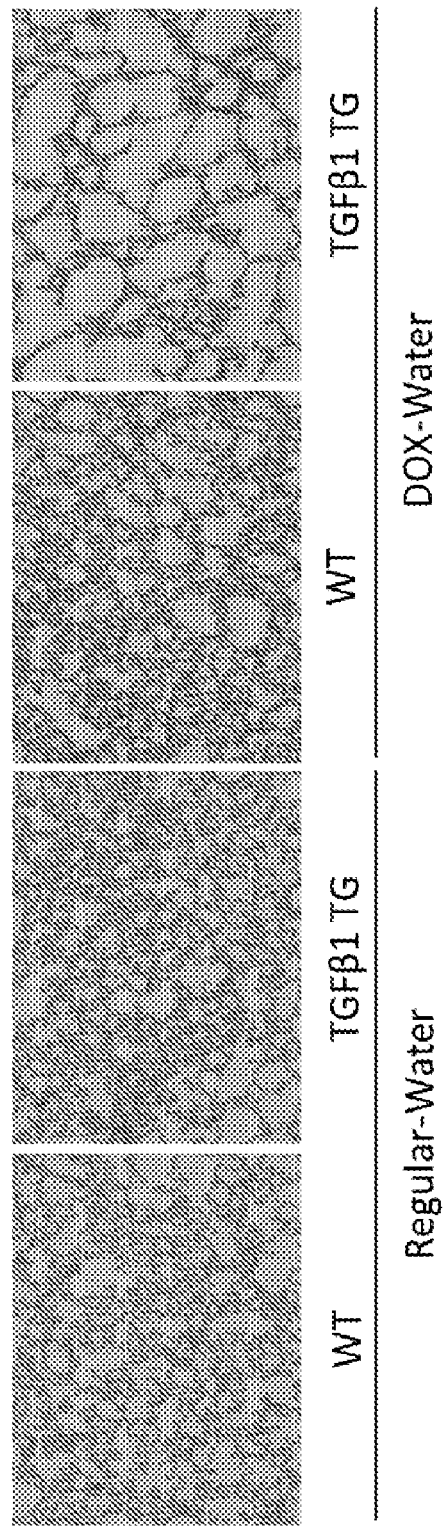
FIG. 11 is a panel of images showing lung histology and morphometry in newborn WT mice and TGF1 transgenic mice (TGF1 TG) treated with water or DOX to induce expression of TGF1 which mimics the BPD mouse model at PN1 4 as well as human BPD.
Figure 12A:
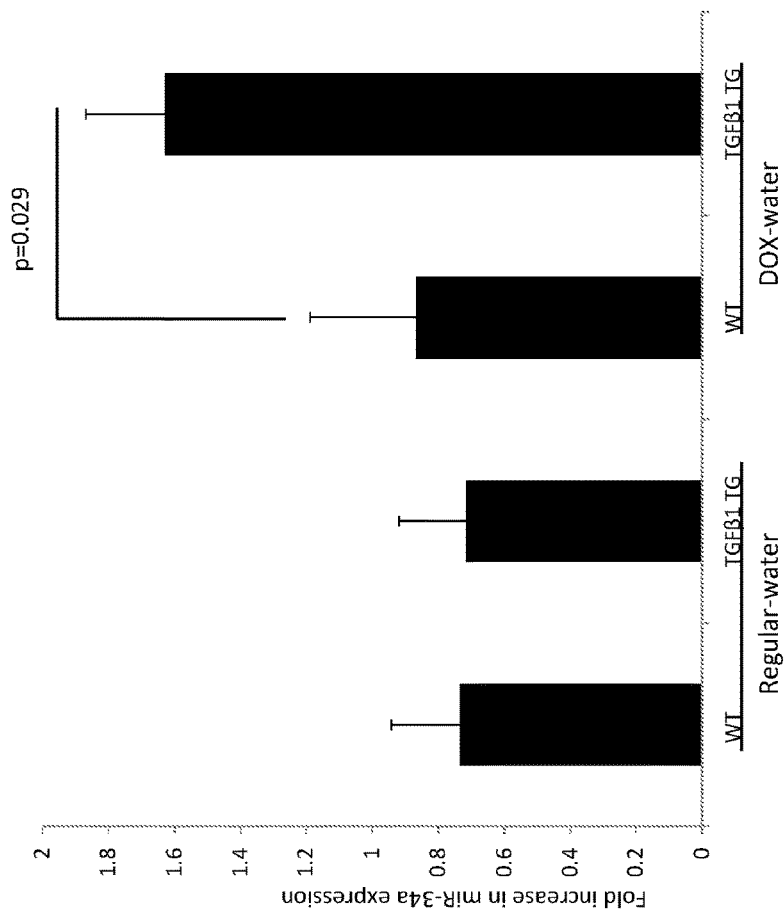
FIG. 12A is a graph showing increased levels of miR34a expression in the lungs of TGF 1 TG mice treated with DOX to induce expression of TGF 1 as compared to WT mice treated with water or DOX or TGF1 TG mice treated with water.
Figure 12B:
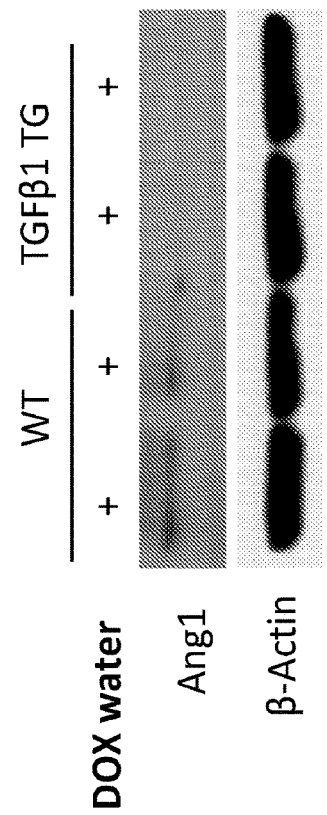
FIG. 12B is a Western Blot showing that the expression of Ang1 is decreased in the TGF1 TG mice treated with DOX to induce expression of TGF1

The second is transforming growth factor beta 1 (TGF1) inducible transgenic mice which were treated with DOX to induce TGF1. TGF1 induction in newborn mice pups from postnatal stage PN7 to PN10, a timeframe that corresponds to the early alveolar stage of lung development and is equivalent to human premature infants at 28-32 weeks of gestation, when the process of developing BPD is well under way. When mice were sacrificed at PN10, the lungs had a clearcut BPD phenotype, FIG. 11. The lungs of these mice had increased levels of miR34a expression (FIG. 12A) and decreased Ang1 expression (FIG. 12B), indicative of the potential role of miR34a in an additional mouse model of BPD.

The biological activity and efficacy of siRNA targeted against interferon-gamma (IFN-y), transforming growth factor-beta 1(TGF-1) and Angiopoietin 2 (Ang2), using RNAse-free water or surfactant (Curosurf®) as the vehicle, in an in vitro system was also of interest. An intranasal delivery of siRNA targeting IFN-y, TGF-1 and Ang2 to newborn (NB) mice lungs in the hyperoxia-induced mouse model of BPD and in lung-specific doxycycline-inducible IFN-y, TGF-1 and Ang2 overexpressing transgenic (TG) mice was tested.

Utilizing developmentally-appropriate mouse models, a hyperoxia-induced and lung-specific doxycycline-inducible IFN-y and TGF 1 TG BPD models described above were used. Ang2 shows significant association with BPD in multiple independent cohorts of human BPD. Also a lung-specific doxycycline-inducible model of Ang2 expression has a pulmonary phenotype characteristic of BPD.

Targeting these cytokines early in the course of the disease may ameliorate the lung phenotype of BPD. Efficacy of utilizing siRNA approaches has been demonstrated in adult mice models. Experiments described herein demonstrate the feasibility of such an approach in the newborn (NB) mouse lung.

For in vivo testing, a hyperoxia induced mouse model of BPD was used. An optimized dose of siRNA singly or in combination intranasally with surfactant (such as Curosurf®) as the vehicle (or RNAse-free water as control) was delivered to the NB mouse on postnatal (PN) days 1 and 3. Since the half-life of siRNA is ~36 hours and in the model, the hyperoxia exposure is from PN1-4, this dosing protocol was sufficient. For the lung specific doxycycline-inducible models of IFN-y, TGF-1 and Ang2, the dosing protocol was adjusted for administration on PN days 1, 3, and 5. These NB mice specific induce gene expression with exposure to doxycycline on PN1, and by PN7 (at sacrifice), their lungs have the BPD phenotype. The efficacy of delivery and biological activity of the IFN-y, TGF-1 and Ang2 were evaluated by measuring mRNA and protein expression in the lung by real-time RT-PCR, western blot and double immunohistochemical staining (using SP-B/C as the marker for Type II pneumocytes) in the three models. The pulmonary phenotype was assessed by lung morphometry, bronchoalveolar lavage (BAL) cell counts, cytokine analysis, histology, TUNEL assay (for cell death), and mRNA and protein expression of vascular and cell death mediators.

The phenomenon of gene silencing expression via RNA interference is dependent on effective transfection of siRNA. Hence, the efficacy of surfactant (such as Curosurf®) was assessed as a transfection reagent with fluorescent-labeled scrambled siRNA. Other transfection reagents, such as Lipofectamine 2000®, was used as a positive control as it is known to have a high transfection efficiency. MLE-12 cells, a pulmonary adenocarcinoma cell line with alveolar ell characteristics, were selected as a surrogate for alveolar epithelial cells.

Figure 13:
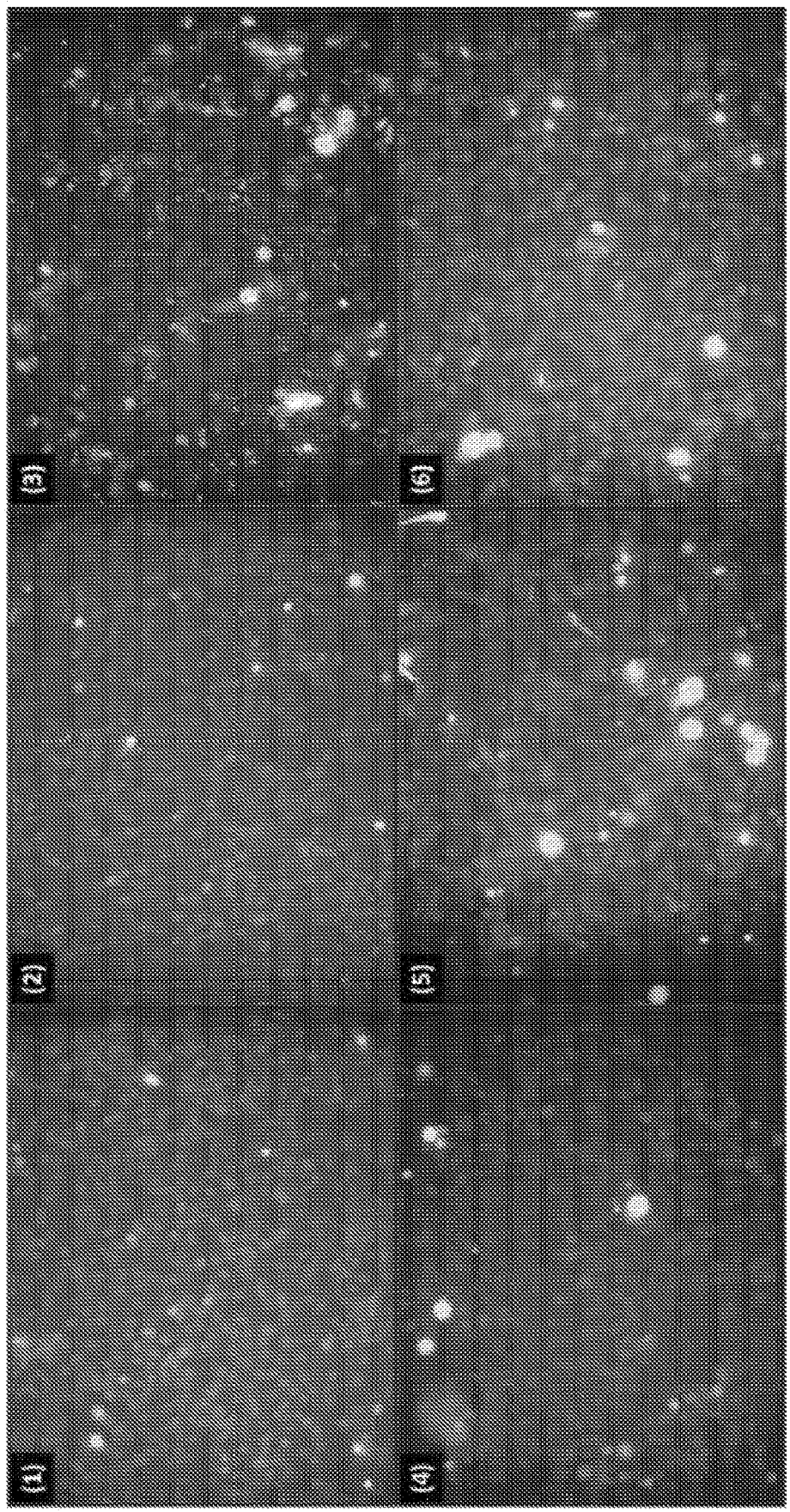
FIG. 13 is a panel of images showing the effect of surfactant on siRNA transfection. Representative fluorescence microscopy images are shown for (1) untreated, (2) scrambled siRNA, (3) siRNA and lipid transfection reagent (Lipofectamine 2000®), (4) siRNA and 5 µL surfactant (Curosurf®), (5) siRNA and 10 µL surfactant (Curosurf®), and (6) siRNA and 20 µL surfactant (Curosurf®). Red areas indicate presence of siRNA.
Figure 14:
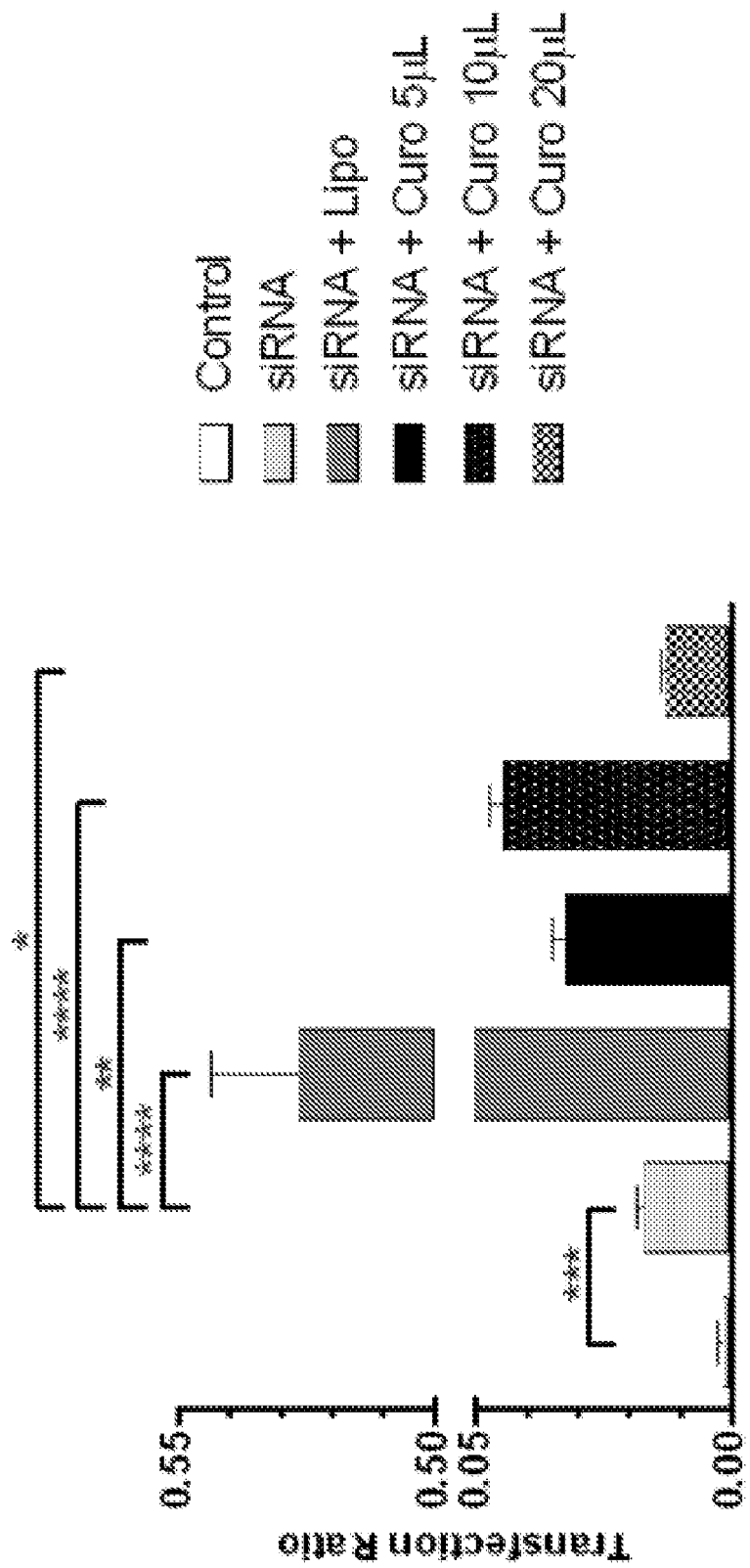
FIG. 14 is a graph showing transfection ratios for each group. Each bar represents the mean±the SEM for a minimum of 3 samples per group. *P:S 0.05, P:S 0.01, *P:S 0.001, ****P:S 0.0001, unpaired t-test. (Curo=Curosurf®, Lipo=Lipofectamine2000®).

As expected, immunofluorescent analysis revealed that detection of scrambled siRNA within cells was dependent on the use of a transfection reagent (FIG. 13). Lipofectamine 2000® had a transfection rate of 53%, over a 30-fold increase in efficiency when compared to siRNA alone (P:S 0.0001; FIG. 14). Among the surfactant groups, cells treated with 10 μL had the highest transfection rate at 4.5% (P:S 0.0001; FIG. 14). Cells treated with 20 μL of surfactant (Curosurf®) actually had a slight decrease in transfection efficiency when compared to siRNA alone (P<0.05; FIG. 14). Taken together, these studies show that at proper concentrations Curosurf® is an enhancer of siRNA transfection in alveolar epithelial cells.

Figure 15:
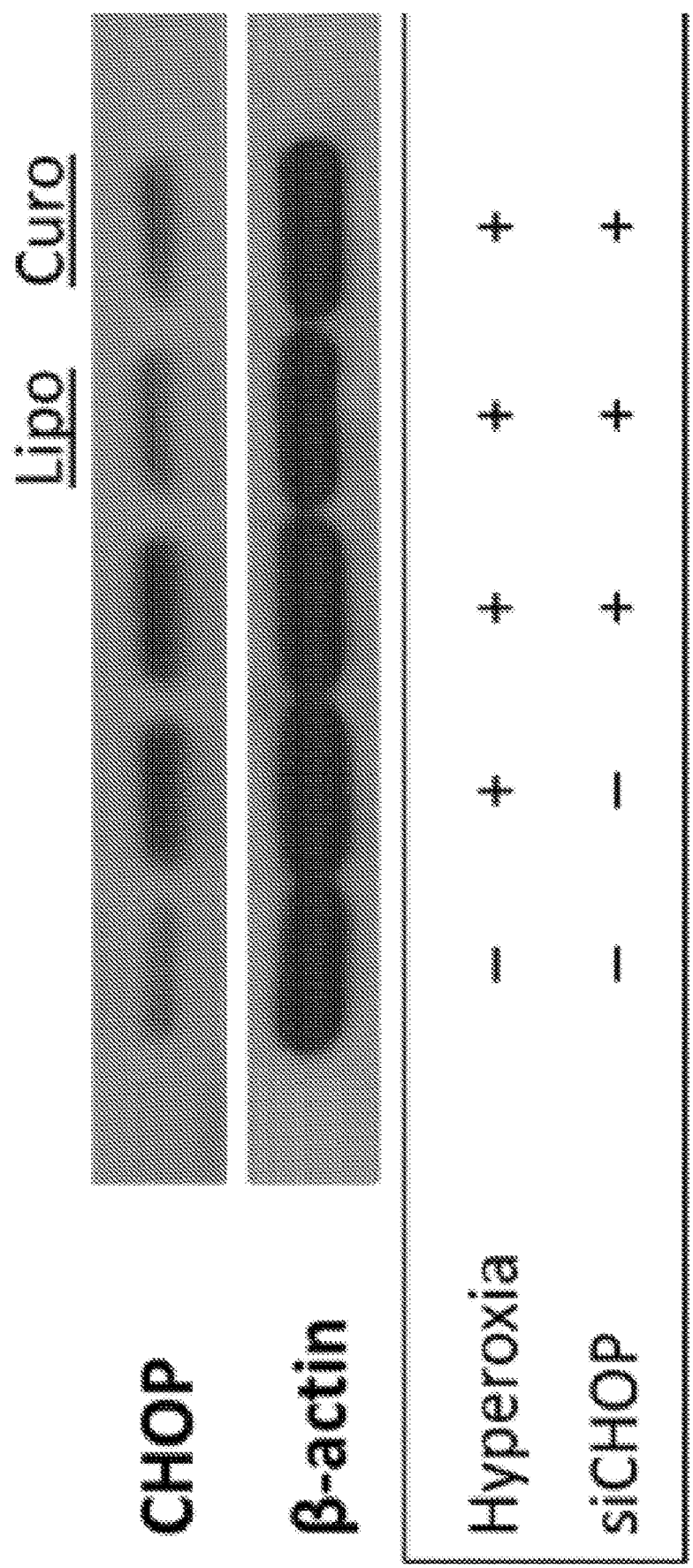
FIG. 15 is a Western Blot showing the in vitro effect of surfactant (Curosurf®) as a transfection reagent on C/EBP homologous protein (CHOP; also known as growth arrest and DNA damage-inducible gene 153/GADD153) expression in hyperoxic exposure. The protein expression of CHOP in MLE-12 cells was ascertained under the conditions described, using -actin as a control.
Figure 16:
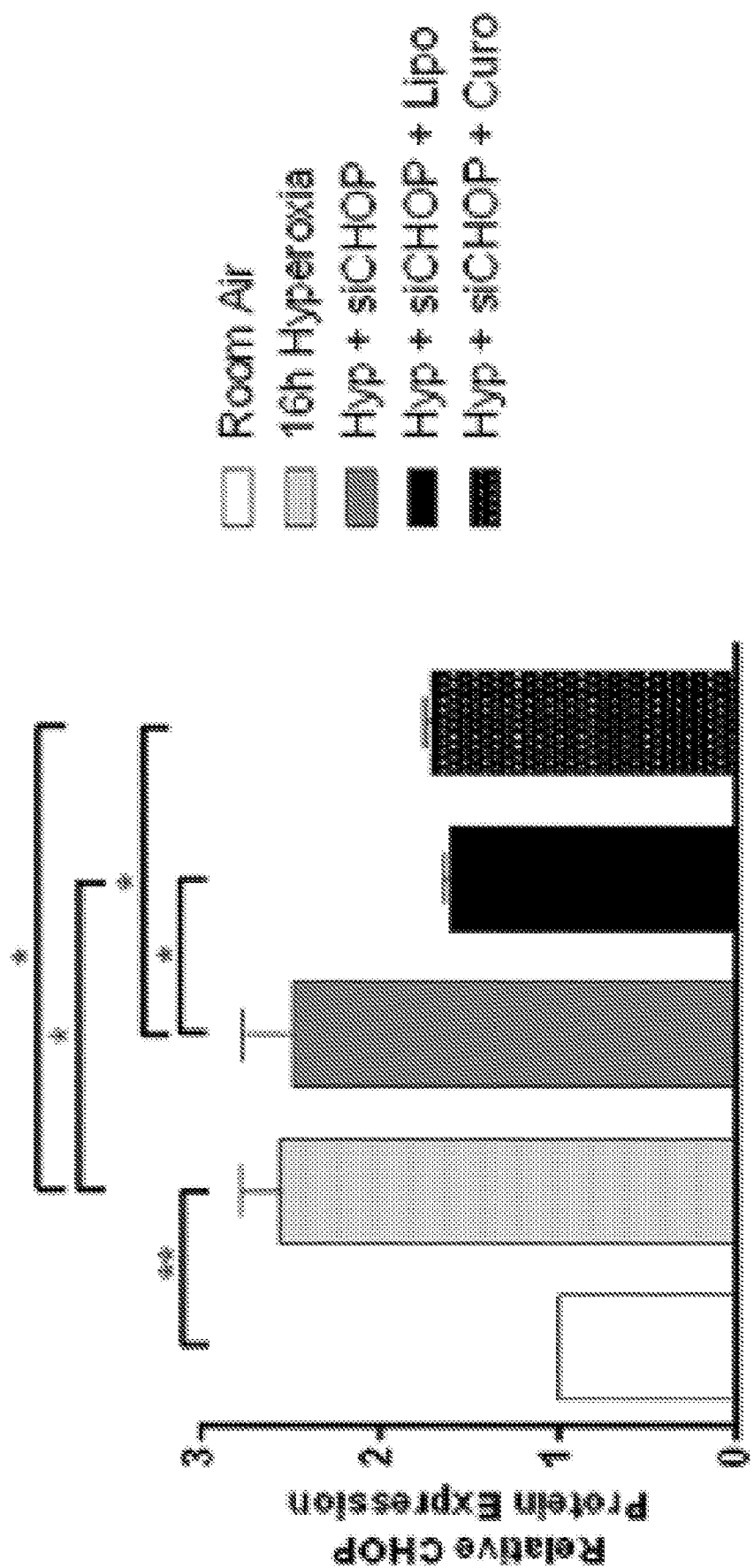
FIG. 16 is a graph showing the corresponding relative CHOP protein expression in MLE-12 cells. Each bar represents the mean±the SEM for a minimum of 3 samples per group. *P:S 0.05, **P:S 0.01, unpaired t-test. (Curo=Curosurf®, Hyp=hyperoxia, Lipo=Lipofectamine 2000®, siCHOP=CHOP siRNA).

Hyperoxia exposure to the developing lung (in mouse and humans) leads to increased IFN-y levels and activation of the endoplasmic reticulum (ER) stress pathway; a key component of the ER stress pathway is the C/EBP homologous protein (CHOP; also known as growth arrest and DNA damage-inducible gene 153/GADD153). Elevated levels of CHOP are associated with cell death via the ER stress-dependent pathway in the hyperoxia-induced model of BPD. To evaluate the use of surfactant (Curosurf®) to augment gene silencing using CHOP siRNA, CHOP protein expression was assessed by western blot analysis (FIG. 15). Exposure to hyperoxia resulted in an increase in CHOP when compared to room air. Both Lipofectamine 2000® and Curosurf® treated groups benefited from a decrease in CHOP protein expression when compared to untreated hyperoxia and naked siRNA (P:S 0.05; FIG. 16). There was no difference between the Curosurf® and Lipofectamine 2000® treated groups, suggesting comparable efficiency in gene silencing. Interestingly, there was no appreciable difference between hyperoxia and naked siRNA groups. Thus, when used as a transfection reagent, Curosurf® serves as a potent enhancer of CHOP gene silencing via RNA interference.

Figure 17:
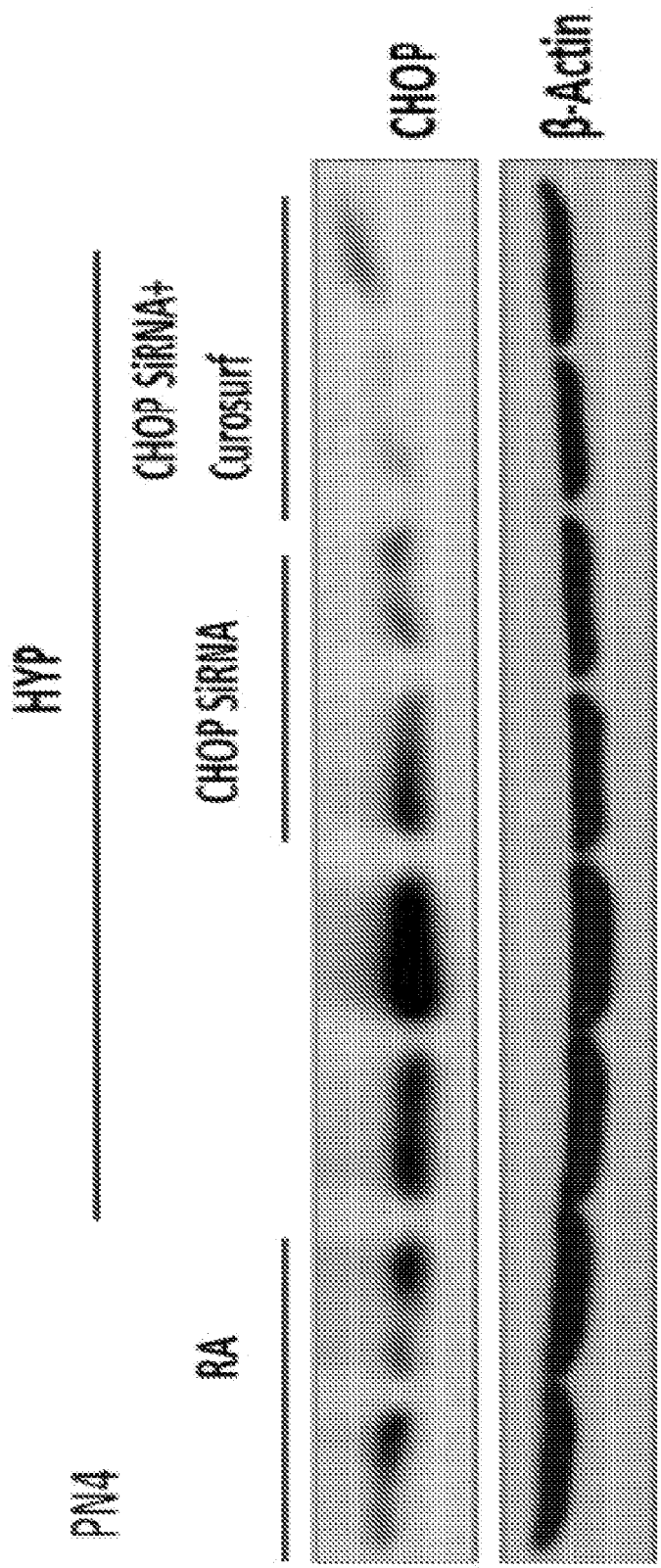
FIG. 17 is a Western Blot showing CHOP expression after siRNA was delivered intranasally on PN1 and PN3 to newborn WT mice (C57B16/J strain) during room air (RA) or hyperoxia (HYP) exposure for 4 days. In the hyperoxia-exposed mice, an additional group was administered CHOP siRNA with surfactant (Curosurf®) as the delivery vehicle. The specificity of the CHOP siRNA-induced decrease in CHOP protein expression, with surfactant (Curosurf®) as the delivery vehicle in hyperoxia, was confirmed by using scrambled siRNA controls
Figure 18:
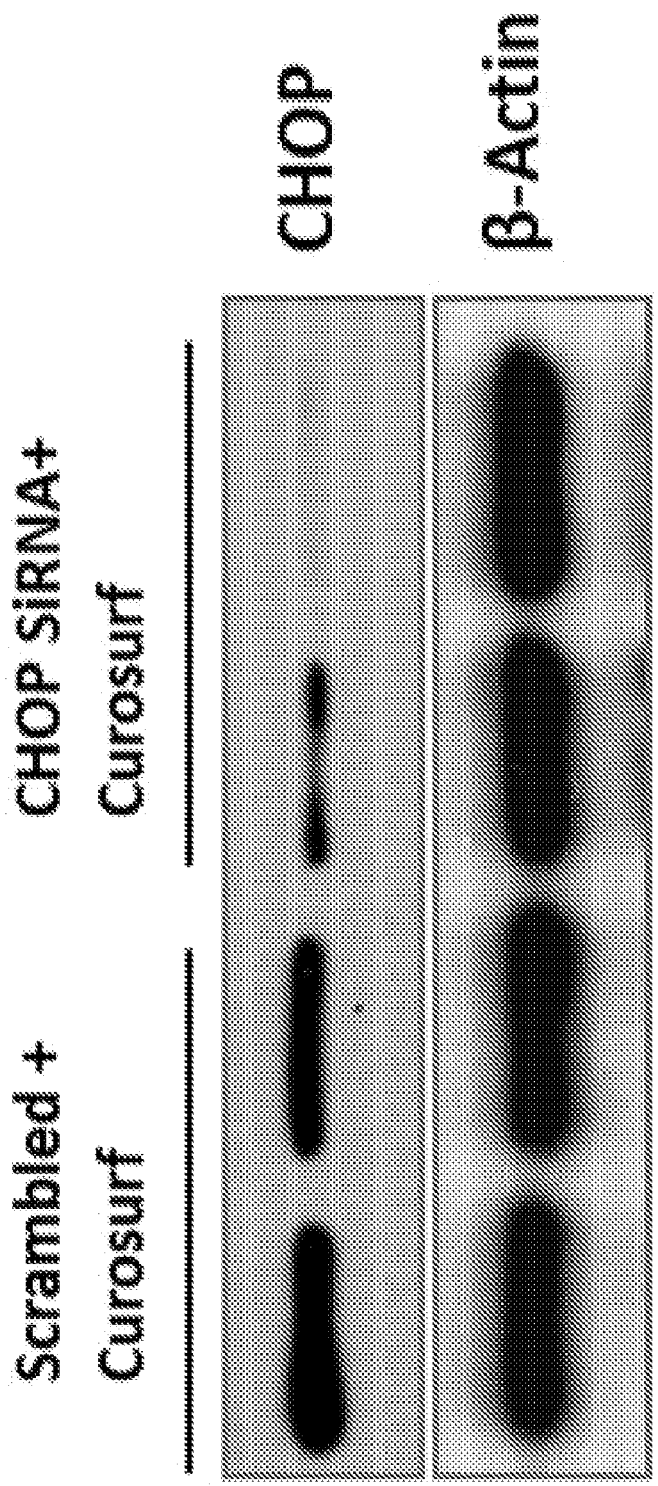
FIG. 18 is a Western Blot showing CHOP protein expression after CHOP or scrambled siRNA was delivered intranasally with surfactant (Curosurf®) as the delivery vehicle on PN1 and PN3 to newborn WT mice (C57B16/J strain) during room air (RA) or hyperoxia (HYP) exposure for 4 days. -actin expression was used as a control.

The use of siRNA against the ER stress pathway mediator, CHOP, has been shown to alleviate cell death in alveolar epithelial cells as well as in hyperoxia-induced and IFN-γ-mediated murine models of BPD. In addition, CHOP siRNA also restored alveolarization in the in vivo models. Hence, it was determined if surfactant-enhanced (Curosurf®) CHOP siRNA delivery would further suppress CHOP protein expression in the hyperoxia-induced mouse model of BPD. To test this, CHOP siRNA was delivered with or without surfactant, as the delivery vehicle, at postnatal (PN) day 1 and 3, and the expression of CHOP protein was evaluated at PN4. The results are shown in FIGS. 17 and 18. The beneficial effects of surfactant-enhanced (Curosurf®) CHOP siRNA were confirmed with lung histology and mophometry in the hyperoxia-exposed BPD model as shown in FIGS. 19A-19B.

Figure 20:
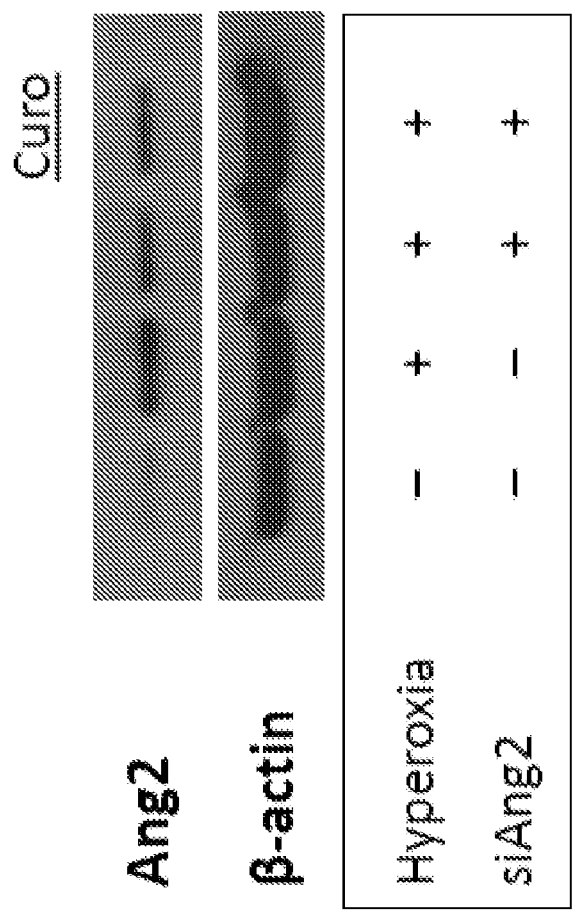
FIG. 20 is a Western Blot showing the in vitro effect of surfactant (Curosurf®) as a transfection reagent on Angiopoietin 2 (Ang2) expression in hyperoxic exposure. The protein expression of Ang2 in MLE-12 cells was ascertained under the conditions described, using actin as a control. (Curo=Curosurf®, siAng2=Ang2 siRNA).
Figures 21A, 21B:
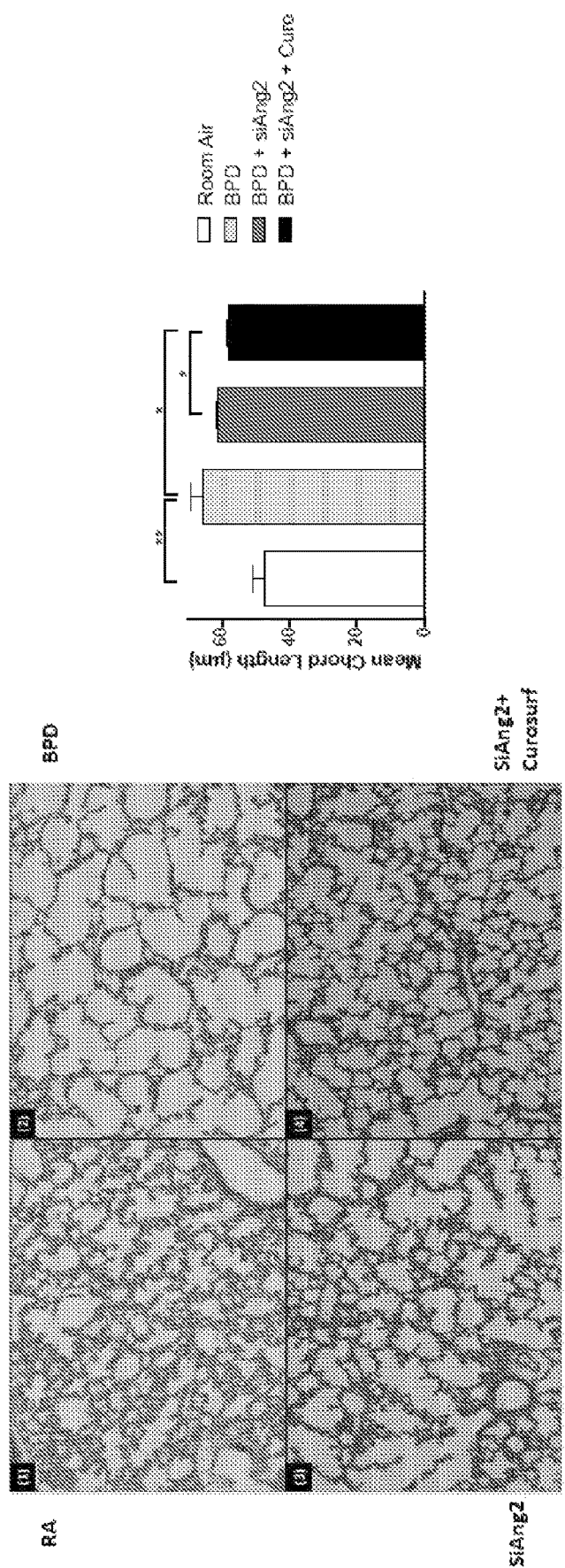
FIG. 21A is a panel of images showing lung histology in newborn WT mice administered Ang2 siRNA alone or with surfactant (Curosurf®) as the delivery vehicle in the BPD mouse model at PN14. Ang2 siRNA with or without surfactant was delivered intranasally on PNI, with repeat doses on PN3 and PN4. Control mice were kept in RA from birth until PN14. Representative photomicrographs of mouse lungs (H&E stain) at PN14 are shown at low-magnification (10×).
FIG. 21B is a graph showing lung morphometry (chord length) in newborn WT mice administered Ang2 siRNA alone or with surfactant (Curosurf®) as the delivery vehicle in the BPD mouse model at PN14. Ang2 siRNA was delivered intranasally on PNI, with repeat doses on PN3 and PN4. Control mice were kept in RA from birth until PN14. *P:S 0.05, **P:S 0.01. RA: room air; Curo=Curosurf®; siAng2: Ang2 siRNA.

Curosurf® also served as a potent enhancer of Ang2 gene silencing via RNA interference in vitro and in vivo as noted in FIGS. 20 and 21A-21B, respectively. FIG. 20 shows similar efficacy with gene silencing with Ang2 siRNA with or without surfactant. Surfactant-enhanced (Curosurf®) Ang2 siRNA delivery was significantly more effective than Ang2 siRNA alone in improving lung histology (FIG. 21A) and morphometry (chord length; FIG. 21B). hyperoxia-induced mouse model of BPD.

In summary, FIGS. 13 and 14 established the optimal dosing regimen to be used when combining surfactant, such as Curosurf®, with siRNA. It is important to keep in mind that the transfection efficiency with lipid reagents, such as Lipofectamine, is exceedingly high, toxicity of such agents have precluded them from being used in in vivo studies. FIGS. 15 and 16 show that combining CHOP siRNA with surfactant has equivalent efficiency in suppressing CHOP expression as combining CHOP siRNA with Lipofecatmine; both approaches being more efficient than naked CHOP siRNA. Finally, as noted in FIG. 17, CHOP expression was markedly increased with hyperoxia exposure, and decreased with CHOP siRNA delivery. When using surfactant as the delivery vehicle, there was a further decrease in CHOP protein expression. Using surfactant as the delivery vehicle did not negatively impact on the specificity of the response, as shown in FIG. 18. Surfactant-enhanced delivery of CHOP and Ang2 improved the BPD lung architecture, with a more significant effect in the latter case, compared to the respective siRNAs alone, as shown in FIGS. 19 and 21A-21B.

Thus, it appears that surfactant, as the delivery vehicle, appears to enhance the effective delivery and distribution of specific siRNA in vitro as well as in vivo in the lung, without impacting on the specificity of the response.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating or preventing a disorder in a lung of a subject comprising:
    administering a therapeutically effective amount of a non-polymeric composition formulated for delivery to a lung tissue comprising a small interfering RNA (siRNA) capable of inhibiting expression of a hyperoxia-induced gene selected from the group consisting of a CHOP siRNA, an Ang2 siRNA, and an anti-sense made against the mature miRNA34a sequence, and a surfactant which comprises a phospholipid, protein SP-B and protein SP-C, to the lung of the subject.

2. The method of claim 1, wherein the siRNA comprises an RNA that inhibits expression of at least one gene encoding a protein selected from the group consisting of C/EBP homologous protein (CHOP), interferon-gamma (IFN-γ), transforming growth factor-beta 1 (TGF-β1), and angiopoietin 2 (Ang2).

3. The method of claim 1, wherein the subject has respiratory distress syndrome and bronchopulmonary dysplasia.

4. A method of treating bronchopulmonary dysplasia in a lung of a subject comprising:
    administering a therapeutically effective amount of a non-polymeric composition formulated for delivery to a lung tissue comprising a small interfering RNA (siRNA) capable of inhibiting expression of a hyperoxia-induced gene selected from the group consisting of a CHOP siRNA, an Ang2 siRNA, and an anti-sense made against the mature miRNA34a sequence, and a surfactant, to the lung of the subject, wherein the siRNA is selected from the group consisting of SEQ ID NO: 1, SEQ ID NO:2, and SEQ ID NO:3.

5. A method of treating bronchopulmonary dysplasia in a lung of a subject comprising:
    administering a therapeutically effective amount of a non-polymeric composition formulated for delivery to a lung tissue comprising a small interfering RNA (siRNA) capable of inhibiting expression of a hyperoxia-induced gene selected from the group consisting of a CHOP siRNA, an Ang2 siRNA, and an anti-sense made against the mature miRNA34a sequence, and a surfactant, to the lung of the subject, wherein the siRNA is an antagomir.

6. The method of claim 5, wherein the siRNA is a miR34a antagomir.

7. A method of treating bronchopulmonary dysplasia in a lung of a subject comprising:
    administering a therapeutically effective amount of a non-polymeric composition formulated for delivery to a lung tissue comprising a small interfering RNA (siRNA) capable of modulating expression of a hyperoxia-induced gene selected from the group consisting of an RNA that modulates expression of at least one gene encoding an anti-inflammatory protein, said at least one gene being selected from the group consisting of Sirt1, Bcl2, Ang1, Tie2, Akt, DLL1, Notch1, Notch2, CDK4, Cyclin D1, caspase 3, caspase 8, caspase 9, Fas, and Fas-L.

8. The method of claim 1, wherein the phospholipid comprises phosphatidylcholine or derivatives thereof.

9. The method of claim 1, wherein the composition is formulated for intranasal administration.

10. The method of claim 1, wherein the composition is formulated for administration by inhalation.

11. The method of claim 10, further comprising administering an inhibitor of cox-2.

12. The method of claim 1, wherein the subject is a human infant or human child.

13. The method of claim 1, wherein the administration delivers the composition to alveoli in the lung.

14. The method of claim 1, further comprising a step of assessing dysregulated vascularization in the lung.

15. The method of claim 1, wherein the subject has bronchopulmonary dysplasia.

16. The method of claim 1, wherein the subject also has hyperoxia-induced cell death in the lung.

17. The method of claim 1, wherein each milliliter of the surfactant comprises 99 weight percent of polar lipids and 1 weight percent of proteins SP-B and SP-C.

18. The method of claim 1, wherein the surfactant is an extract of a natural porcine lung surfactant.

19. The method of claim 1, wherein the subject has respiratory distress syndrome.

20. The method of claim 1, wherein the subject is a premature human infant.

21. The method of claim 1, wherein the subject has hyperoxia-induced cell death in the lung.

* * * * *